US012799079B2

(12) United States Patent
Dhanoa

(10) Patent No.: US 12,799,079 B2
(45) Date of Patent: Nov. 17, 2026

(54) DEUTERIUM-ENRICHED 3,5-DIMETHYLPYRAZOLYL-3-PROPOXY-4-FLUOROBENZOIC ACIDS FOR TREATMENT OF TRANSTHYRETIN AMYLOIDOSIS CARDIOMYOPATHY (ATTR-CM) AND POLYNEUROPATHY (ATTR-PN), AND RELATED DISEASES

(71) Applicant: Daljit Singh Dhanoa, Del Mar, CA (US)

(72) Inventor: Daljit Singh Dhanoa, Del Mar, CA (US)

( * ) Notice: Subject to any disclaimer, the term of this patent is extended or adjusted under 35 U.S.C. 154(b) by 242 days.

(21) Appl. No.: 18/956,885

(22) Filed: Nov. 22, 2024

(65) Prior Publication Data

US 2025/0179026 A1 Jun. 5, 2025

Related U.S. Application Data

(60) Provisional application No. 63/604,356, filed on Nov. 30, 2023.

(51) Int. Cl.
*C07D 231/12* (2006.01)
*A61K 31/415* (2006.01)

(52) U.S. Cl.
CPC .......... *C07D 231/12* (2013.01); *A61K 31/415* (2013.01)

(58) Field of Classification Search
None
See application file for complete search history.

(56) References Cited

U.S. PATENT DOCUMENTS 9,169,214 B2 * 10/2015 Graef .................. A61K 31/415

OTHER PUBLICATIONS

Pirali, et al., J. Med. Chem., 62:5276. (Year: 2019).*

* cited by examiner

*Primary Examiner* — Michael Barker

(57) ABSTRACT

The present invention is concerned with novel deuterium-enriched compounds of the general chemical structural formula I, and pharmaceutically acceptable salts, compositions, and methods of use thereof, wherein, R is independently deuterium (D), hydrogen (H) atom. Compounds of the general chemical structure formula I are stabilizers of the Transthyretin (TTR) protein and are useful in the treatment of Transthyretin Amyloidosis cardiomyopathy (ATTR-CM) and Polyneuropathy (ATTR-PN), and related diseases.

1

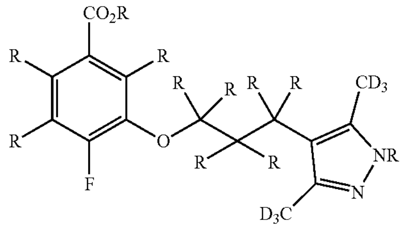

R = D, H

13 Claims, No Drawings

DEUTERIUM-ENRICHED 3,5-DIMETHYLPYRAZOLYL-3-PROPOXY-4-FLUOROBENZOIC ACIDS FOR TREATMENT OF TRANSTHYRETIN AMYLOIDOSIS CARDIOMYOPATHY (ATTR-CM) AND POLYNEUROPATHY (ATTR-PN), AND RELATED DISEASES

PRIORITY CLAIM

This application is a continuation-in-part of U.S. Provisional Patent Application No. 63/604,356 which is incorporated by reference in its entirety for all purposes.

FIELD OF THE INVENTION

This invention relates to disclosing novel deuterium-enriched compounds, pharmaceutical salts, compositions and methods of use thereof for stabilizing a protein namely transthyretin, inhibiting transthyretin misfolding, fibrils formation, aggregation and deposition of amyloid fibrils into various organs and tissues including heart, lung, kidney, liver, brain, and nervous system, and thereby treating transthyretin-mediated diseases, including transthyretin amyloidosis (ATTR) and other related diseases associated thereto.

BACKGROUND OF THE INVENTION

Transthyretin (TTR) is a 55 kDa homotetrameric protein abundantly present in serum and cerebrospinal fluid (CSF), Transthyretin (TTR) is a tetrameric protein produced in the liver that serves as a plasma transport protein carrying thyroxine and retinol. In patients with transthyretin amyloidosis (ATTR), unstable tetramer structure of thyretin protein (TTR) may dissociate due to genetic mutation (e.g. V122I mutation) or age and misfold into amyloid fibrils. These fibrils can then deposit in various tissues and/or organs throughout the body, leading to a constellation of symptoms. Transthyretin amyloidosis (ATTR) has two types, hereditary or wild type. Hereditary transthyretin amyloidosis (hATTR) is inherited in an autosomal dominant manner with variable penetrance. Mutations in the TTR gene lead to the formation of abnormal proteins. Wild-type ATTR (ATTRwt) develops with age and is acquired when normal TTR tetramers destabilize and become amyloidogenic.

$ATTR_{WT}$ classically is present with cardiomyopathy, carpal tunnel syndrome, and radiculopathy in older patients, usually above the age of 60 years. hATTR amyloidosis is seen in younger (early-onset) and older patients (late-onset), resulting in peripheral neuropathy, cardiomyopathy, or a mixed combination. The phenotypes vary depending on the mutation.

Post-secretion amyloidogenesis of plasma TTR requiring rate limiting tetramer dissociation, monomer misfolding and misassembly putatively causes familial amyloid cardiomyopathy and the familial amyloid polyneuropathies, and senile systemic amyloidosis.

The TTR amyloid diseases include but are not limited to familial amyloid cardiomyopathy, familial amyloid polyneuropathy, leptomeningeal amyloids, oculoleptomengial amyloidosis, senile systemic amyloidosis, vitreous amyloidosis, and CNS amyloidosis. Amyloid diseases also include but are not restricted to ocular amyloidosis, gastrointestinal amyloidoses, neuropathic amyloidoses, non-neuropathic amyloidoses, nephropathy, non-hereditary amyloidoses, reactive/secondary amyloidoses, cerebral amyloidoses, Alzheimer's disease, spongiform encephalopathy (i.e. Creutzfeldt Jakob disease, GSS, fatal familial insomnia), frontotemporal dementia, Parkinson's disease, amyotrophic lateral sclerosis (ALS), Down Syndrome, multiple sclerosis, polyneuropathy, Guillain-Barré syndrome, macular degeneration, vitreous opacities, glaucoma, type II diabetes and medullary carcinoma of the thyroid.

General and non-invasive interventions to ameliorate TTR amyloidosis (ATTR) preferably by orally active drugs are in great need to treat ATTR and related diseases.

TTR is a 55 kDa tetramer composed of 127 amino-acid subunits exhibiting an unusually high β-sheet content. It possesses a conserved structural prototype of four identical monomeric subunits that form a central channel or binding site [Gasperini R. J., et al. Mechanisms of transthyretin aggregation and toxicity, *Subcell. Biochem.* 2012, 65, 211-224; Kelly J. W., et al. Transthyretin quaternary and tertiary structural changes facilitate misassembly into amyloid. *Adv. Protein. Chem.* 1997, 50, 161-181].

Structural changes in amyloidogenic TTR have been difficult to identify through X-ray crystallography; however, novel studies with nuclear magnetic resonance spectroscopy have revealed small chemical shifts to the backbone structure of mutated and WT-TTR [Leach B. I., Zhang X., Kelly J. W., Dyson H. J., Wright P. E. NMR Measurements reveal the structural basis of transthyretin destabilization by pathogenic Mutations. *Biochemistry.* 2018, 57, 4421-4430]. These changes are significant to the TTR ground state and the most significant changes were found in proximity to the site of the mutation. These subtle structural differences are just one consequence of the mutation, and different TTR variants might experience diverse structural deformation pathways, resulting in atypical responses to the cellular conditions or proteolytic stress.

ATTR-CM and ATTR-PN are rare, progressive and underdiagnosed ATTR-mediated potentially fatal diseases. Effective therapeutics are unavailable for the treatment or prevention of transthyretin amyloidosis (ATTR) and ATTR-mediated diseases. The present invention discloses novel deuterium-containing compounds that stabilize TTR dissociation and prevent TTR aggregation and provide therapeutics for the prevention and treatment of transthyretin amyloidosis (ATTR) and ATTR-mediated cardiomyopathy (ATTR-CM) and related ATTR-mediated diseases.

SUMMARY OF THE INVENTION

The present invention is concerned with novel deuterium-enriched compounds of the general chemical structural formula I, and pharmaceutically acceptable salts, compositions, and methods of use thereof,

1

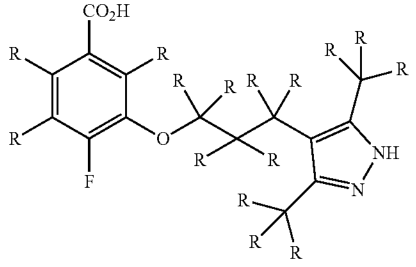

wherein,

R is independently deuterium (D).

Compounds of chemical structural formula I are stabilizers of the tetrameric protein, Transthyretin (TTR), thereby these deuterium-enriched compounds of formula I can prevent TTR dissociation and its subsequent aggregation, and deposition in organs and tissues, including heart, lungs, kidney, liver, brain, nervous system, and thereby treat Transthyretin Amyloidosis (ATTR) and ATTR-mediated diseases.

The compounds of formula I, and their pharmaceutical salts are Transthyretin (TTR) stabilizers, and are useful for the treatment of diseases mediated by TTR including Transthyretin Amyloidosis (ATTR) and related diseases.

Transthyretin Amyloidosis (ATTR) is a systemic, progressive, debilitating and life-threatening disease with a constellation of clinical manifestations. Transthyretin Amyloidosis (ATTR) is caused by formation, aggregation, and deposition of amyloid fibrils from destabilization of the tetrameric TTR in different organs and tissues including heart and nervous system and other organs including kidneys, resulting in end organ damage and their dysfunction. Transthyretin (TTR) amyloidosis is an under diagnosed disease that is characterized by misfolding of TTR and aggregation as amyloid fibrils, predominantly leading to transthyretin amyloidosis cardiomyopathy (ATTR-CM) or transthyretin amyloidosis polyneuropathy (ATTR-PN) depending on the particular TTR mutation. Transthyretin amyloid cardiomyopathy (ATTR-CM) can also occur as an age-related disease caused by misfolding of wild-type TTR.

Deuterium-enriched Compounds of formula I disclosed in the present invention are oral transthyretin (TTR) stabilizers for the treatment of transthyretin amyloidosis (ATTR) diseases including but not limited to transthyretin amyloidosis cardiomyopathy (ATTR-CM) and transthyretin amyloidosis polyneuropathy (ATTR-PN). Significant unmet medical need exists for prevention and/or treatment of ATTR-mediated diseases including ATTR-CM, ATTR-PN, and other diseases.

In this invention, we disclose the design and synthesis of highly potent and selective novel compounds as Transthyrin (TTR) stabilizers that can treat transthyretin amyloidosis (ATTR) diseases including but not limited to transthyretin amyloidosis cardiomyopathy (ATTR-CM) and transthyretin amyloidosis polyneuropathy (ATTR-PN).

These novel deuterium-enriched compounds of formula I and pharmaceuticals salts thereof can also treat leptomeningeal amyloids, oculoleptomengial amyloidosis, senile systemic amyloidosis, vitreous amyloidosis, and CNS amyloidosis. Amyloid diseases also include but are not restricted to ocular amyloidosis, gastrointestinal amyloidoses, neuropathic amyloidoses, non-neuropathic amyloidoses, nephropathy, non-hereditary amyloidoses, reactive/secondary amyloidoses, cerebral amyloidoses, Alzheimer's disease, spongiform encephalopathy (i.e. Creutzfeldt Jakob disease, GSS, fatal familial insomnia), frontotemporal dementia, Parkinson's disease, amyotrophic lateral sclerosis (ALS), Down Syndrome, multiple sclerosis, polyneuropathy, Guillain-Barré syndrome, macular degeneration, vitreous opacities, glaucoma, type II diabetes and medullary carcinoma of the thyroid.

This invention further constitute a method for stabilizing tetrameric structure of the transthyretin (TTR) protein preventing from its dissociation into its monomeric forms leading to protein misfolding and formation, aggregation, and deposition of amyloid fibrils in organs and tissues, thereby causing transthyretin amyloidosis (ATTR) in mammal, including humans, which comprises administering to a mammal in need of such treatment an effective amount of a compound of structural Formula I and pharmaceuticals salts thereof.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference in their entirety. In case of conflict, the present application, including definitions, will control. In addition, the materials, methods, and examples are illustrative only and not intended to be limiting.

Other features and advantages of the invention will be apparent from the following detailed description, and from the claims.

DETAILED DESCRIPTION OF THE INVENTION

The present invention relates to novel deuterium-enriched compounds of general chemical structural formula I, and pharmaceutically acceptable salts, compositions, and methods of use thereof,

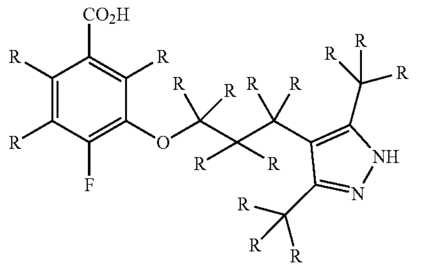

1 wherein,

R is independently deuterium (D).

The compounds of formula I and pharmaceutically acceptable salts and combinations thereof, have activity for stabilizing transthyretin and are therefore useful in the treatment of diseases involving tetrameric transthyretin degradation, aggregation and accumulation of dissociated monomers into fibril deposits in various tissues and organs and thereby leading to their dysfunction and end-organ damage including heart, kidneys, brain and other organs and tissues.

Transthyretin (TTR) is an abundant protein in serum and cerebrospinal fluid (CSF). Transthyretin (TTR) is a tetramer protein produced in the liver that serves as a plasma transport protein carrying thyroxine and retinol. TTR is a 55 kDa tetramer composed of 127 amino-acid subunits exhibiting an unusually high β-sheet content. It possesses a conserved structural prototype of four identical monomeric subunits that form a central channel or binding site [Gasperini R. J., et al. Mechanisms of transthyretin aggregation and toxicity. *Subcell. Biochem.* 2012, 65, 211-224; Kelly J. W., et al. Transthyretin quaternary and tertiary structural changes facilitate misassembly into amyloid. *Adv. Protein. Chem.* 1997, 50, 161-181].

Pathogenic mutations accelerate TTR aggregation by thermodynamic or kinetic destabilization of the protein [Hammerstrom, P., et al, *Proc. Natl, Acad. Sci. U.S.A,* 2002, 99, 16427-16432]; Hurshman, A. R., et al. *Biochemistry* 2008, 47, 6969-694]. Familial amyloid cardiomyopathy (FAC) and Familial amyloid polyneuropathy (FAP) are the most prevalent ATTR diseases affecting the heart and peripheral nervous system, respectively [Jacobson, D. R., et al. *N. Eng. J. Med.* 1997, 336, 466-473; Andrade, C. A., Brain, 1952, 75, 408-427; Saraiva, M. *J., J. Clin. Invest.* 1984, 74, 104-119]. Rare mutations are involved in the central nervous system [Goren, H., et al. *Brain* 1980, 103, 473-495; Sekijima, Y., et al. *Lab Invest.* 2003, 83, 409-417]. FAC and FAP are also called transthyretin amyloidosis cardiomyopathy (ATTR-CM) and transthyretin amyloidosis polyneuropathy (ATTR-PN) respectively.

In patients with transthyretin amyloidosis (ATTR), unstable tetrameric structure of thyretin protein (TTR) may dissociate due to genetic mutation (e.g. V122I mutation) or age, and misfolding into amyloid fibrils. These fibrils can then deposit in various tissues and/or organs throughout the body, leading to a constellation of symptoms. Transthyretin Amyloidosis (ATTR) is caused by formation, aggregation, and deposition of amyloid fibrils from destabilization of the tetrameric TTR in different organs and tissues including heart and nervous system and other organs including kidneys, resulting in end organ damage and their dysfunction.

Transthyretin amyloidosis (ATTR) has two types, hereditary or wild type. Hereditary transthyretin amyloidosis (hATTR) is inherited in an autosomal dominant manner with variable penetrance. Mutations in the TTR gene lead to the formation of abnormal proteins. Wild-type ATTR (ATTRwt) develops with age and is acquired when normal TTR tetramers destabilize and become amyloidogenic. $ATTR_{WT}$ classically is present with cardiomyopathy, carpal tunnel syndrome, and radiculopathy in older patients, usually above the age of 60 years. hATTR amyloidosis is seen in younger (early-onset) and older patients (late-onset), resulting in peripheral neuropathy, cardiomyopathy, or a mixed combination. The phenotypes vary depending on the mutation.

General and non-invasive interventions to ameliorate TTR amyloidosis (ATTR) preferably by orally active drugs are of great interest and tremendous need for addressing unmet need to treat ATTR and related diseases.

Traditional drugs such as beta-blockers, angiotensin-converting enzyme inhibitors (ACEI), or angiotensin receptor antagonists/blockers (ARB) for symptomatic treatment, cannot slow, halt, or reverse the underlying cause of ATTR-CM.

The novel deuterium-enriched compounds disclosed in this invention are effective kineic stablizers of TTR that inhibit dissociation of the non-amyloidogenic native state of TTR protein. The stabilization of the native state of TTR by compounds of formula I also can treat neurodegerative diseases since misfolded oligomers have been reported to cause neurodegeneration.

Deuterium-enriched Compounds of formula 1 disclosed in the present invention are oral transthyretin (TTR) stabilizers for the treatment of transthyretin amyloidosis (ATTR) diseases including but not limited to transthyretin amyloidosis cardiomyopathy (ATTR-CM) and transthyretin amyloidosis polyneuropathy (ATTR-PN). Significant unmet medical need exists for prevention and/or treatment of ATTR-mediated diseases including ATTR-CM, ATTR-PN, and other diseases.

In this invention, we disclose the design and synthesis of highly potent and selective novel compounds as Transthyrin (TTR) stabilizers that can treat transthyretin amyloidosis (ATTR) diseases including but not limited to transthyretin amyloidosis cardiomyopathy (ATTR-CM) and transthyretin amyloidosis polyneuropathy (ATTR-PN).

These novel deuterium-enriched compounds of formula I and pharmaceuticals salts thereof can also treat leptomeningeal amyloids, oculoleptomengial amyloidosis, senile systemic amyloidosis, vitreous amyloidosis, and CNS amyloidosis. Amyloid diseases also include but are not restricted to ocular amyloidosis, gastrointestinal amyloidoses, neuropathic amyloidoses, non-neuropathic amyloidoses, nephropathy, non-hereditary amyloidoses, reactive/secondary amyloidoses, cerebral amyloidoses, Alzheimer's disease, spongiform encephalopathy (i.e. Creutzfeldt Jakob disease, GSS, fatal familial insomnia), frontotemporal dementia, Parkinson's disease, amyotrophic lateral sclerosis (ALS), Down Syndrome, multiple sclerosis, polyneuropathy, Guillain-Barré syndrome, macular degeneration, vitreous opacities, glaucoma, type II diabetes and medullary carcinoma of the thyroid.

Deuterium (D or $^2H$) is a stable non-radioactive isotope of hydrogen (H) and has an atomic weight of 2.0144. Hydrogen occurs naturally as a mixture of the isotopes $^1H$, D ($^2H$ or deuterium), and T ($^3H$ or tritium) and the natural abundance of deuterium is 0-015%. One of ordinary skill in the art recognizes that in all compounds containing H atom, H actually represents a mixture of H and D, with about 0-015% of D. So therefore, compounds with a level of D (deuterium) that has been enriched to be greater than its natural abundance of 0.015%, should be considered unnatural and as a result novel as compared to their corresponding non-enriched counterparts.

The carbon-hydrogen bonds contain a naturally occurring distribution of hydrogen isotopes, namely $^1H$ or protium (about 99.9844%), $^2H$ or deuterium (D) (about 0.0156%), and $^3H$ or tritium (in the range between about 0.5 and 67 tritium atoms per 1018 protium atoms). Higher levels of deuterium incorporation produce a detectable Kinetic Isotope Effect [Werstiuk, N. H.; Dhanoa, D. S.; Timmins, G. *Can J. Chem.* 1979, 57, 2885; Werstiuk, N. H.; Dhanoa, D. S.; Timmins, G. *Can J. Chem.* 1983, 61, 2403], that could improve the pharmacokinetic, pharmacologic and/or toxicologic parameters of compounds of formula I in comparison to compounds having naturally occurring levels of deuterium and their corresponding hydrogen (protium) analogs.

Suitable modifications of certain carbon-hydrogen (C—H) bonds into carbon-deuterium (C-D) bonds can generate novel substituted compounds of structural formula I with unexpected and non-obvious improvements of pharmacological, pharmacokinetic and toxicological properties in comparison to the non-isotopically enriched compounds. This invention relies on the judicious and successful application of chemical kinetics to drug design. Deuterium incorporation levels in the compounds of the invention are significantly higher than the naturally-occurring levels and are sufficient to induce at least one substantial improvement as described herein.

"Deuterium enrichment" refers to the percentage of incorporation of deuterium at a given site on the molecule instead of a hydrogen atom. For example, deuterium enrichment of 1% means that in 1% of molecules in a given sample a particular site is occupied by deuterium. Because the naturally occurring distribution of deuterium is about 0.0156%, deuterium enrichment in compounds synthesized using non-enriched starting materials is about 0.0156%.

It can be a significant synthetic challenge to produce 100% deuterium at a specific site of a compound. High levels of deuterium content in a compound can be produced either by Hydrogen-Deuterium (H-D) exchange or by synthesizing the compound for specific deuteration. The H-D exchange is readily achieved in case of H atoms attached to heteroatoms for example in cases of carboxylic acids (COOH), sulfonamides ($SO_2NH_2$, $CONHSO_2$-aryl, $CONHSO_2$-alkyl), alcohols (OH), basic amines ($NH_2$), etc. However, these incorporated deuterium (D) attached to heteroatoms (O, N, S) readily revert back to hydrogen (H) upon exposure to water or any acidic compounds containing H atoms. The preferred deuterium containing compounds contain deuterium (D) directly attached to carbon atoms of the structure of the compounds of this present invention.

In some embodiments, the deuterium enrichment in the compounds of the present invention is greater than 4%, 5%, 6%, 7%, 8%, 9% or 10%. In other embodiments, the deuterium enrichment in the compounds of the present invention is greater than 20%. In further embodiments, the deuterium enrichment in the compounds of the present invention is greater than 50%. In some embodiments, the deuterium enrichment in the compounds of the present invention is greater than 70%. In some embodiments, the deuterium enrichment in the compounds of the present invention is greater than 90%.

The present invention relates to novel deuterium-enriched compounds of general chemical structural formula I, and pharmaceutically acceptable salts, compositions, and methods of use thereof,

1

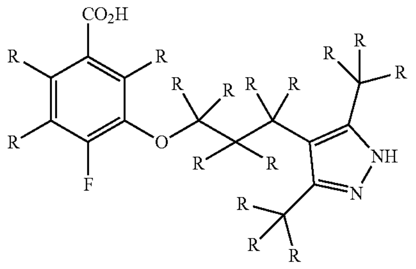

wherein,

R is independently deuterium (D).

Wherein D is deuterium atom present in the compounds of formula I and about 1%-100% enrichment of deuterium is incorporated.

In some embodiments, a compound of the invention is of the chemical structural formula of I,

1

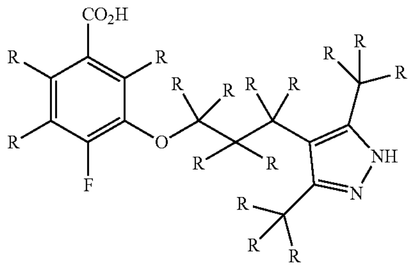

and pharmaceutically acceptable salts, compositions, and methods of use thereof, wherein, R is independently deuterium (D).

In another embodiments, a compound of the present invention is a deuterium-enriched compound, and pharmaceutically acceptable salts, compositions, and methods of use thereof, of name and formula:

(a)

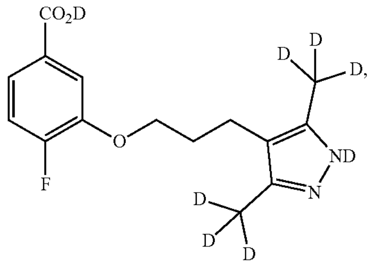

3-(3-(3,5-bis(methyl-$d_3$)-1H-pyrazol-4-yl-1-d)propoxy)-4-fluorobenzoic acid-d (b)

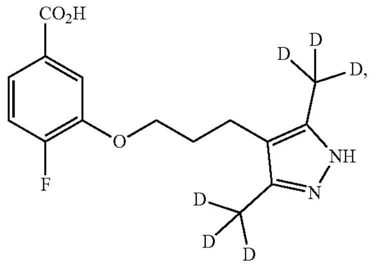

3-(3-(3,5-bis(methyl-$d_3$)-1H-pyrazol-4-yl)propoxy)-4-fluorobenzoic acid (c)

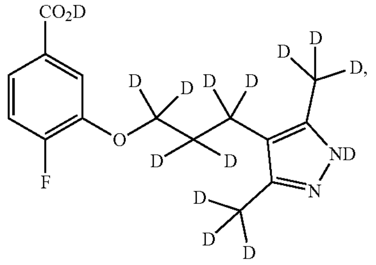

3-(3-(3,5-bis(methyl-$d_3$)-1H-pyrazol-4-yl-1-d)propoxy-1,1,2,2,3,3-$d_6$)-4-fluorobenzoic acid-d (d)

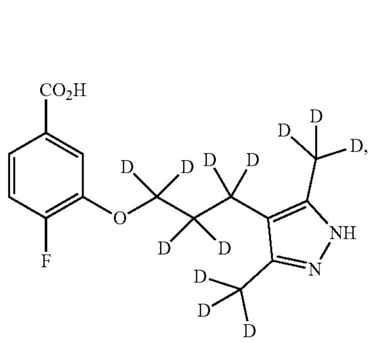

3-(3-(3,5-bis(methyl-$d_3$)-1H-pyrazol-4-yl)propoxy-1,1,2,2,3,3-$d_6$)-4-fluorobenzoic acid -continued (e)

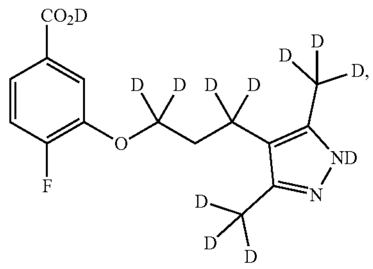

3-(3-(3,5-bis(methyl-$d_3$)-1H-pyrazol-4-yl-1-d)propoxy-1,1,3,3-$d_4$)-4-fluorobenzoic acid-d (f)

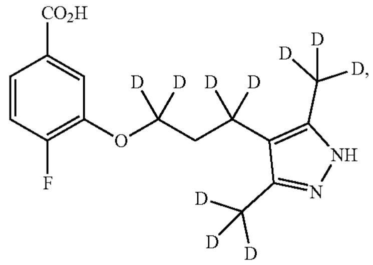

3-(3-(3,5-bis(methyl-$d_3$)-1H-pyrazol-4-yl)propoxy-1,1,3,3-$d_4$)-4-fluorobenzoic acid (g)

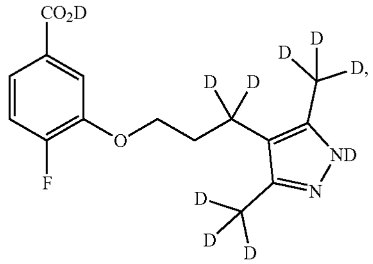

3-(3-(3,5-bis(methyl-$d_3$)-1H-pyrazol-4-yl-1-d)propoxy-3,3-$d_2$)-4-fluorobenzoic acid-d (h)

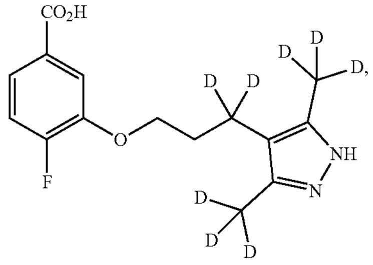

3-(3-(3,5-bis(methyl-$d_3$)-1H-pyrazol-4-yl)propoxy-3,3-$d_2$)-4-fluorobenzoic acid -continued (i)

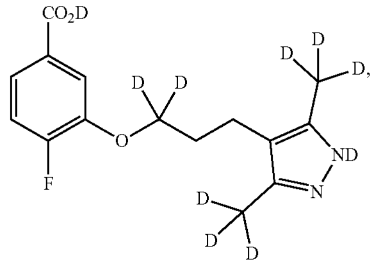

3-(3-(3,5-bis(methyl-$d_3$)-1H-pyrazol-4-yl-1-d)propoxy-1,1-$d_2$)-4-fluorobenzoic acid-d (j)

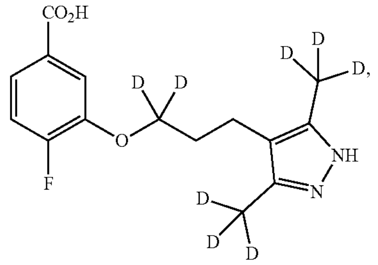

3-(3-(3,5-bis(methyl-$d_3$)-1H-pyrazol-4-yl)propoxy-1,1-$d_2$)-4-fluorobenzoic acid (k)

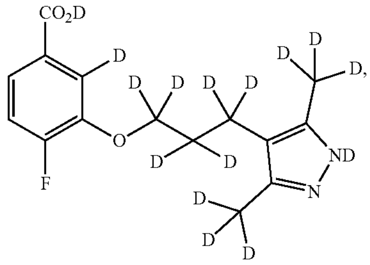

3-(3-(3,5-bis(methyl-$d_3$)-1H-pyrazol-4-yl-1-d)propoxy-1,1,2,2,3,3-$d_6$)-4-fluorobenzoic-2-d acid-d (l)

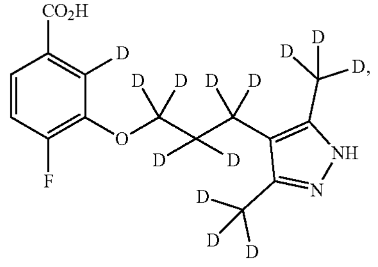

3-(3-(3,5-bis(methyl-$d_3$)-1H-pyrazol-4-yl)propoxy-1,1,2,2,3,3-$d_6$)-4-fluorobenzoic-2-d acid -continued (m)

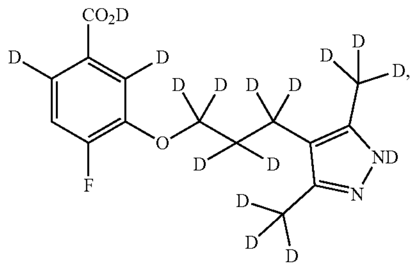

3-(3-(3,5-bis(methyl-$d_3$)-1H-pyrazol-4-yl-1-d)propoxy-1,1,2,2,3,3-$d_6$)-4-fluorobenzoic-2,6-$d_2$ acid-d (n)

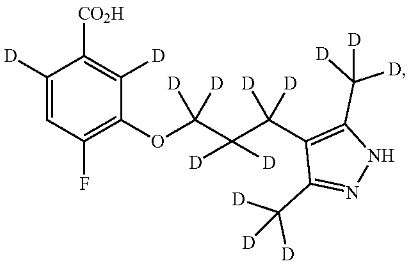

3-(3-(3,5-bis(methyl-$d_3$)-1H-pyrazol-4-yl)propoxy-1,1,2,2,3,3-$d_6$)-4-fluorobenzoic-2,6-$d_2$ acid (o)

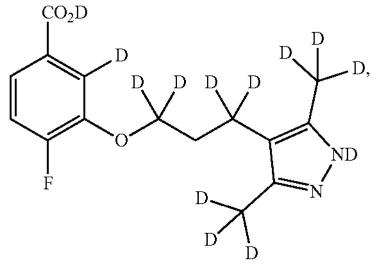

3-(3-(3,5-bis(methyl-$d_3$)-1H-pyrazol-4-yl-1-d)propoxy-1,1,3,3-$d_4$)-4-fluorobenzoic-2-d acid-d (p)

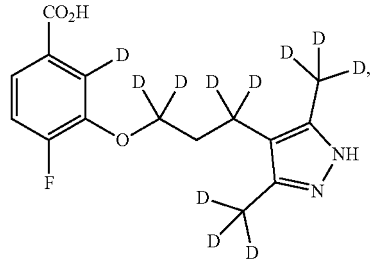

3-(3-(3,5-bis(methyl-$d_3$)-1H-pyrazol-4-yl)propoxy-1,1,3,3-$d_4$)-4-fluorobenzoic-2-d acid -continued (q)

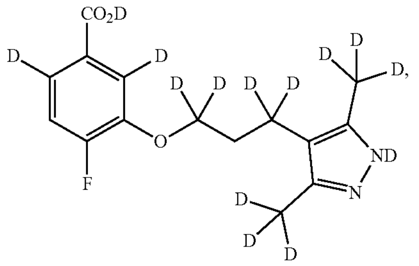

3-(3-(3,5-bis(methyl-$d_3$)-1H-pyrazol-4-yl-1-d)propoxy-1,1,3,3-$d_4$)-4-fluorobenzoic-2,6-$d_2$ acid-d (r)

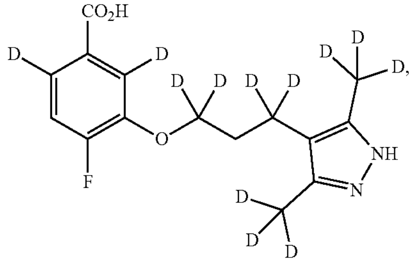

3-(3-(3,5-bis(methyl-$d_3$)-1H-pyrazol-4-yl)propoxy-1,1,3,3-$d_4$)-4-fluorobenzoic-2,6-$d_2$ acid In another embodiment, a pharmaceutical composition comprising a compound of the invention of formula I in an amount effective for the treatment of a disease selected from transthyretin amyloidosis cardiomyopathy (ATTR-CM) and transthyretin amyloidosis polyneuropathy (ATTR-PN), leptomeningeal amyloids, oculoleptomengial amyloidosis, senile systemic amyloidosis, vitreous amyloidosis, and CNS amyloidosis, ocular amyloidosis, gastrointestinal amyloidosis, neuropathie amyloidosis, non-neuropathic amyloidosis, nephropathy, non-hereditary amyloidosis, reactive/secondary amyloidosis, cerebral amyloidosis, Alzheimer's disease, spongiform encephalopathy (i.e. Creutzfeldt Jakob disease, GSS, fatal familial insomnia), frontotemporal dementia, Parkinson's disease, amyotrophic lateral sclerosis (ALS), Down Syndrome, multiple sclerosis, polyneuropathy, Guillain-Barré syndrome, macular degeneration, vitreous opacities, glaucoma, type II diabetes and medullary carcinoma of the thyroid.

In another embodiment, a method of treating a disease selected from transthyretin amyloidosis cardiomyopathy (ATTR-CM) and transthyretin amyloidosis polyneuropathy (ATTR-PN), leptomeningeal amyloids, oculoleptomengial amyloidosis, senile systemic amyloidosis, vitreous amyloidosis, and CNS amyloidosis, ocular amyloidosis, gastrointestinal amyloidosis, neuropathic amyloidosis, non-neuropathic amyloidosis, nephropathy, non-hereditary amyloidosis, reactive/secondary amyloidosis, cerebral amyloidosis, Alzheimer's disease, spongiform encephalopathy (i.e. Creutzfeldt Jakob disease, GSS, fatal familial insomnia), frontotemporal dementia, Parkinson's disease, amyotrophic lateral sclerosis (ALS), Down Syndrome, multiple sclerosis, polyneuropathy, Guillain-Barré syndrome, macular degeneration, vitreous opacities, glaucoma, type II diabetes and medullary carcinoma of the thyroid, comprising administering a pharmaceutically effective amount of a pharmaceutical composition of compound of formula I.

In another embodiment, the compounds of the invention described herein may also be administered in combination with other treatments for diseases caused by TTR amyloid. Treatments for diseases caused by TTR amyloid include heart transplant for TTR cardiomyopathy, liver transplant, other kinetic stabilizers of TTR, RNA knock-down and/or RNA interference methods and the like. The compound described herein the present invention of formula I may be administered before, after, or during another treatment or medical procedure including heat transplant for TTR cardiomyopathy, liver transplant, other stabilizer molecules, entities, for diseases caused by TTR amyloid.

In some embodiments, the compounds and compositions of the present invention, disclosed herein may be administered as the only therapeutic agent or in combination with other active ingredients. The compounds and compositions may be administered in combination with other compounds to treat amyloidosis and amyloid disorders, including but not limited to compounds, for example, that bind to and stabilize TTR and/or compounds that target TTR RNA and/or compounds that modulate the expression of the TTR protein and/or compounds that modulate the transcription of the TTR gene and/or compounds, which may modulate intra or extracellular protein homeostasis and/or protein stability and/or protein aggregation and/or protein folding.

Further active ingredients for combination treatments and/or therapies include but are not limited to compounds for the disease modifying or symptomatic treatment of amyloidosis, including but not limited to familial amyloid polyneuropathy, familial amyloid cardiomyopathy, cerebral amyloidosis, leptomeningeal amyloids, oculoleptomengial amyloidosis, senile systemic amyloidosis, vitreous amyloidosis, ocular amyloidosis, gastrointestinal amyloidosis, neuropathic amyloidosis, non-neuropathic amyloidosis, nephropathy, non-hereditary amyloidosis, reactive/secondary amyloidosis, Alzheimer's disease, spongiform encephalopathy (i.e. Creutzfeldt Jakob disease, GSS, fatal familial insomnia), Guillain-Barré syndrome, frontotemporal dementia, multiple sclerosis, polyneuropathy, Parkinson's disease, amyotrophic lateral sclerosis (ALS), Down Syndrome, macular degeneration, vitreous opacities, glaucoma, type II diabetes and medullary carcinoma of the thyroid.

The reaction scheme conceptualized and used for the synthesis of compounds and intermediates of this invention are general. It will be understood by those skilled in the art of organic synthesis that one or more functional groups present in a given compound of the invention may render the molecule incompatible with a particular synthetic sequence. In such a case an alternative synthetic route, an altered order of steps or a strategy of protection and deprotection may be employed. The reactions are performed in a solvent appropriate to the reagents and materials employed and suitable for the transformation being effected. It is understood by those skilled in the art of organic synthesis that the functionality present on the reactants and reagents being employed should be consistent with the chemical transformations being conducted. Depending upon the reactions and techniques to be used optimal yields may require changing the order of synthetic steps or use of protecting groups followed by deprotection. In all cases the particular reaction conditions, including reagents, solvent, temperature and time, should be chosen so that they are consistent with the nature of the functionality present in the molecule.

The compounds useful in the novel method treatment of this invention may form salts with various inorganic and organic acids and bases, which are also within the scope of the invention. Such salts include alkali metal salts like sodium and potassium salts, ammonium salts, alkaline earth metal salts such as calcium and magnesium salts, salts with organic bases for example dicyclohexylamine salts, N-methyl-D-glucamine salts, salts with amino acids e.g., arginine, lysine, etc. In addition, salts with organic and inorganic acids may be prepared; e.g., HCl, HBr, $H_2SO_4$, $H_3PO_4$, methanesulfonic, toluenesulfonic, maleic, fumaric, camphorsulfonic acid.

The salts can be formed by conventional means, such as by reacting the free acid or free base forms of the product with one or more equivalents of the appropriate base or acid in a solvent or medium in which the salt is insoluble, or in a solvent such as water, which is then removed in vacuo or by freeze-drying or by exchanging the cations of an existing salt for another cation on a suitable ion exchange resin.}

The compounds useful in the novel method treatment of this invention form solvates with various solvents, which are also within the scope of the invention. Such solvates include methyl tert-butyl ether solvates, diethyl ether or others.

It will be appreciated that the compounds of general Formula I in this invention may be derivatized at functional groups to provide prodrug derivatives, which are capable of conversion back to the parent compounds in vivo. The concept of prodrug administration has been extensively reviewed (e.g. A. A. Sinkula in *Annual Reports in Medicinal Chemistry*, Vol 10, R. V. Heinzelmann, ED., Academic Press, New York, London, 1975, Ch 13, pp 306-326; H. Ferres, Drugs of Today, Vol 19, 499-538, 1983, and *J. Med. Chem.*, 18, 172, 1975). Examples of such prodrugs include the physiologically acceptable and metabolically labile ester derivative, such as lower alkyl (e.g. methyl or ethyl esters), aryl (e.g. 5-indanyl esters), alkenyl (e.g. vinyl esters), alkoxyalkyl (e.g. methoxymethyl esters), alkylthioalkyl (e.g. methylthiomethyl esters), alkanoyloxyalkyl (e.g. pivaloyloxymethyl esters), and substituted or unsubstituted aminomethyl esters (e.g. 2-dimethylaminoethyl esters). Additionally, any physiologically acceptable equivalents of the compounds of general structural formula I, similar to the metabolically labile esters, which are capable of producing the parent compounds of general Formula I in vivo, are within the scope of this invention.

"Therapeutically effective amount" includes an amount of a compound of the present invention that is effective when administered alone or in combination to treat the desired condition or disorder. "Therapeutically effective amount" includes an amount of the combination of compounds claimed that is effective to treat the desired condition or disorder.

The combination of compounds is preferably a synergistic combination. "Pharmaceutically acceptable salts" refer to derivatives of the disclosed compounds wherein the parent compound is modified by making an acid or base salts thereof. Examples of the pharmaceutically acceptable salts include, but not limited to, mineral or organic acid salts of the basic residues. The pharmaceutically acceptable salts include but not limited to HCl, HBr, HI, potassium (K), sodium (Na), calcium (Ca), magnesium (Mg), acetic, trifluoroacetic, citric, ascorbic, benzoin, methanesulfonic (mesylate), benzenesulfonic, bicarbonic, carbonic, ethane disulfonic, edetic, fumaric, maleic, lactic, malic, mandelic, gluconic, glutamic, glycolic, glycollyarsanilic, lauryl, hexylresorcinic, hyrdabamic, hydroxymaleic, hydroxynaphthoic, isethionic, lactobionic, napsylic, nitric, oxalic, pamoic, pantothenic, phenyllacetic, phosphoric, polygalacturonic, propionic, salicyclic, stearic, subacetic, succinic, sulfamic, sulfanilic, sulfuric, tannic, tartaric, tolouenesulfonic, and p-bromobenzenesulfonic.

Definitions

For purposes of the present invention, as described and claimed herein, the following terms are defined as follows:

As used herein, the terms "comprising" and "including" are used in their open, non-limiting sense. The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above.

The phrase "pharmaceutically acceptable salt(s)", as used herein, unless otherwise indicated, includes salts of acidic or basic groups, which may be present in the compounds of formula I. The compounds of formula I that are basic in nature are capable of forming a wide variety of salts with various inorganic and organic acids. The acids that may be used to prepare pharmaceutically acceptable acid addition salts of such basic compounds of formula I are those that form non-toxic acid addition salts, i.e. salts containing pharmacologically acceptable anions, such as the acetate, benzenesulfonate, benzoate, bicarbonate, bisulfate, bitartrate, borate, bromide, calcium edetate, camsylate, carbonate, chloride, clavulanate, citrate, dihydrochloride, edetate, edislyate, estolate, esylate, ethylsuccinate, fumarate, gluceptate, gluconate, glutamate, glycollylarsanilate, hexylresorcinate, hydrabamine, hydrobromide, hydrochloride, iodide, isothionate, lactate, lactobionate, laurate, malate, maleate, mandelate, mesylate, methylsulfate, mucate, napsylate, nitrate, oleate, oxalate, pamoate (embonate), palmitate, pantothenate, phospate/diphosphate, polygalacturonate, salicylate, stearate, subacetate, succinate, tannate, tartrate, teoclate, tosylate, triethiodode, and valerate salts.

Certain compounds of formula I may have asymmetric centers and therefore exist in different enantiomeric forms. All optical isomers and stereoisomers of the compounds of formula I and mixtures thereof, are considered to be within the scope of the invention. With respect to the compounds of formula I the invention includes the use of a racemate, one or more enantiomeric forms, one or more diastereomeric forms, or mixtures thereof. The compounds of formula I may also exist as tautomers. This invention relates to the use of all such tautomers and mixtures thereof.

Certain functional groups contained within the compounds of the present invention can be substituted for bioisosteric groups, that is, groups which have similar spatial or electronic requirements to the parent group, but exhibit differing or improved physicochemical or other properties. Suitable examples are well known to those of skill in the art, and include, but are not limited to moieties described in Patini et al., *Chem. Rev,* 1996, 96, 3147-3176 and references cited therein.

This invention also encompasses pharmaceutical compositions containing compounds of the formula I. and methods of treating ATTR, and ATTR-mediated diseases through administering prodrugs of compounds of the formula I. Compounds of formula I having carboxylic or amino groupscan be converted into prodrugs. Prodrugs include compounds wherein a carboxyl or an amino group can be derivatized into an easily cleavable group under physiological conditions in the mammals' bodies to enhance drug molecules absorption and increase its therapeutic effect in the subjects (e.g. human).

For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in *Advanced Drug Delivery Reviews,* 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy) methyl and (acyloxy) ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities.

The compounds of the invention can also be used in combination with other drugs. If a compound used in the method of the invention is a base, a desired salt may be prepared by any suitable method known to the art, including treatment of the free base with an inorganic acid (such as hydrochloric acid, hydrobromic acid, sulfuric acid, nitric acid phosphoric acid, and the like), or with an organic acid (such as acetic acid, maleic acid, succinic acid, mandelic acid, fumaric acid, malonic acid, pyruvic acid, oxalic acid, glycolic acid, salicylic acid, pyranosidyl acid (such as glucuronic acid or galacturonic acid), alpha-hydroxy acid (such as citric acid or tartaric acid), amino acid (such as aspartic acid or glutamic acid), aromatic acid (such as benzoic acid or cinnamic acid), sulfonic acid (such as p-toluenesulfonic acid or ethanesulfonic acid}, and the like. In the case of compounds of the present invention, prodrugs, salts, or solvates that are solids, it is understood by those skilled in the art that the hydroxamate compound, prodrugs, salts, and solvates used in the method of the invention, may exist in different polymorph or crystal forms, all of which are intended to be within the scope of the present invention and specified formulas. In addition, the hydroxamate compound, salts, prodrugs and solvates used in the method of the invention may exist as tautomers, all of which are intended to be within the broad scope of the present invention. Solubilizing agents may also be used with the compounds of the invention to increase the compounds solubility in water or physiologically acceptable solutions. These solubilizing agents include cyclodextrans, propylene glycol, diethylacetamide, polyethylene glycol, Tween, ethanol and micelle forming agents. Other solubilizing agents are cyclodextrans, particularly beta cyclodextrans and in particular hydroxypropyl betacyclodextran and sulfobutylether betacyclodextran. In some cases, the compounds, salts, prodrugs used in the method of the invention may exist as solvates. All such solvates, and combinations and mixtures thereof are intended to be within the broad scope of the present invention.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. In a preferred embodiment of the present invention, "treating" or "treatment" means at least the mitigation of a disease condition in a human that is alleviated by the inhibition of the activity related to transthyretin or other related protein, protein misfolding, protein fragments, accumulation, fibril formation, aggregation, and causing any dysfunction and/or damage in and/or to tissues and organs.

The present invention also includes prophylactic methods, comprising administering an effective amount of a compound of the invention, or a pharmaceutically acceptable salt, prodrug, pharmaceutically active metabolite, or solvate thereof to a mammal, such as a human, at risk for infection by a coronavirus. According to certain preferred embodiments, an effective amount of one or more compounds of the invention, or a pharmaceutically acceptable salt, prodrug, pharmaceutically active metabolite, or solvate thereof is administered to a human at risk for cardiovascular, kidney, and nervous system by ATTR. The prophylactic methods of the invention include the use of one or more of the compounds in the invention in any conventionally acceptable manner.

"Therapeutically effective amount" includes an amount of a compound of the present invention that is effective when administered alone or in combination to treat the desired condition or disorder. "Therapeutically effective amount" includes an amount of the combination of compounds claimed that is effective to treat the desired condition or disorder. The combination of compounds is preferably a synergistic combination.

"Pharmaceutically acceptable salts" refer to derivatives of the disclosed compounds wherein the parent compound is modified by making acid or base salts thereof. Examples of the pharmaceutically acceptable salts include, but not limited to, mineral or organic acid salts of the basic residues. The pharmaceutically acceptable salts include but not limited to HCl, HBr, HI, potassium (K), sodium (Na), calcium (Ca), magnesium (Mg), acetic, trifluoroacetic, citric, ascorbic, benzoin, methanesulfonic (mesylate), benzenesulfonic, bicarbonic, carbonic, ethane disulfonic, edetic, fumaric, maleic, lactic, malic, mandelic, gluconic, glutamic, glycolic, glycollyarsanilic, lauryl, hexylresorcinic, hyrdabamic, hydroxymaleic, hydroxynaphthoic, isethionic, lactobionic, napsylic, nitric, oxalic, pamoic, pantothenic, phenyllacetic, phosphoric, polygalacturonic, propionic, salicyclic, stearic, subacetic, succinic, sulfamic, sulfanilic, sulfuric, tannic, tartaric, tolouenesulfonic, and p-bromobenzenesulfonic.

SYNTHESIS OF COMPOUNDS

Preparation of compounds of chemical formula I described below is general. It should be understood by those skilled in the art of chemical synthesis that some functional groups may not be compatible for certain synthetic routes and those cases may require appropriate changes including alternative starting materials, building blocks, intermediates, synthesis, synthetic methods process, appropriate sequence of synthetic steps, and compatible protection and deprotection strategy should be employed. The particular reaction conditions, such as reagents, solvents, temperature, and reaction time, should be used for conducting a synthetic reaction consistent with the nature of the functionality of the reactant and products involved.

The synthesis of the novel deuterium-enriched (deuterated or deuterium-containing) compounds of Formula I of this invention is shown below in Schemes 1-2.

Those skilled in the art will recognize or be able to ascertain using no more than routine experimentation, numerous equivalents to the specific reagents can be utilized to produce compounds of the invention. Numerous modifications and variations of the present invention are possible and therefore it is understood that within the scope of the appended claims, the invention may be practiced otherwise that as specifically described herein. Other aspects, advantages and modifications are within the scope of the invention.

One of the three main building blocks, 4-Fluoro-3-hydroxybenzoic acid 1, for the synthesis of compounds of chemical structural formula I, is heated at reflux conditions with deuterium oxide ($D_2O$ ) and deuterium chloride (DCl) at pD 0.32 (pD is equivalent of pH in case of HCl) for 1 hour to yield the dideuterated 4-Fluoro-3-hydroxybenzoic acid-$d_2$2 as shown in Scheme 1. The deuterated compound 2 is converted into its methyl ester 4 by refluxing 2 in methanol in the presence of a catalytic amount of concentrated sulfuric acid for overnight. Alternatively, 4-Fluoro-3-hydroxybenzoic acid 1 is converted into its methyl ester 3, from which deuterated benzoic acid compound 4 is prepared.

Microwave irradiation (microwave heating) at 180 °C of a mixture of 3, $D_2O$ and concentrated HCl (1 equivalent) in a microwave apparatus for 30 minutes yields deuterated 4-fluoro-3-hydroxybenzoic methyl ester 4. Compound 3 is also transformed into its corresponding deuterated analog compounds by treating methyl 4-fluoro-3-hydroxybenozoate 3 with $D_2O$ and DCl at pD 0.32 under reflux conditions for one hour. Ethyl ester of 4-Fluoro-3-hydroxybenzoic acid is also prepared using same synthetic methods and procedure by using ethyl alcohol ($C_2H_5OH$, Ethanol, EtOH) instead of methanol ($CH_3OH$, methyl alcohol). Ethanol is readily available from commercial sources in its absolute form (100% ethyl alcohol) but tends to be more expensive than its reagent grade ethanol or reagent grade methanol. Both methanol and ethanol can be dried (to remove any trace amounts of water content present in reagent grade $CH_3OH$ or $CH_3CH_2OH$ by various methods routinely used in organic synthesis laboratories).

Second key intermediate compound 5 required for the synthesis of the compounds of formula I of this invention is deuterated 1-3-dibromopropane-d2-6 5, which is prepared from either diethyl malonate 5a ($R_1$=ethyl), dimethyl malonate 5a ($R_1$=methyl), deuterated diethyl malonate-$d_2$5c or dimethyl malonate-$d_2$5c, or malonaldehyde 5e, as shown in Scheme 1. Malonic acid esters 5a are reduced using lithium aluminum deuteride (LiAlD4) in diethyl ether or tetrahydrofuran (THF) at low temperature to produce the corresponding tetradeuterated reduced product, alcohol 5b-$d_4$. Propane-1,3-diol 5b is also synthesized by reduction of malonic esters 5a using diisobutylaluminum deuteride (DIBAL-D) in THF or using DIBAL-D in THF followed by treatment with sodium borodeuteride ($NaBD_4$) to yield propane diol 5b-$d_4$.

Dideuteromalonate esters 5c are prepared from readily available dimethyl malonate or diethyl malonate 5a by treatment of 5a with sodium ethoxide and deuterium oxide (or deuterium water, $D_2O$ ). Dideuterated malonic esters 5c are reduced to the corresponding hexadeuterated 1,3-propane-diol 5d using either $LiALD_4$ or treatment with DIBAL-D and then reduction of resulting aldehyde with $NaBD_4$ to afford 5-$d_6$, as shown in Scheme 1.

Tetradeuterated 1,3-propanediol is also prepared from commercially available malonaldehyde 5e (1,3-propanedialhyde or 1,3-propanal). As shown in Scheme 1, dialdehyde 5e is reduced by treatment of 5e with sodium borodeuteride ($NaBD_4$) to yield 1,1,3,3-deutero-1,3-propanediol 5b-$d_4$.

Deuterated 1,3-propanediol intermediate compounds 5b and 5d are then converted individually to their corresponding deuterated 1,3-dibromopropane derivatives 5-$d_4$ and 5-$d_6$ by their treatment carbon tetrabromide ($CBr_4$) and triphenyl phosphine ($Ph_3P$) in methylene chloride ($CH_2Cl2$)

at 0 °C to room temperature (RT). Dihydroxy intermediate 5b and 5d are also converted into their corresponding dibromides 5-$d_4$ and 5-$d_6$ by treatment with phosphorus triboromide ($PBr_3$) and diethyl ether (or ether, $Et_2O$) as shown in Scheme 1.

Third key intermediate compound needed as building block for the synthesis of the compounds of formula I of this invention is deuterated acetylacetone (2,4-pentanedione-$d_{1-6}$, 8) which is synthesized from acetylacetone 7. Acetylacetone 7 is treated with lithium diisopropyl amide (LDA) in tetrahydrofuran (THF) at −78 °C (dry ice in acetone bath) and deuterium oxide ($D_2O$ ) or deuterium chloride (DCl) to yield highly deutertated acetylacetone 8 as shown in Scheme 1.

5, partially deuterated or undeuterated 1,3-dibormopropane using either anhydrous potassium carbonate ($K_2CO_3$) as a base in acetone under reflux conditions overnight or using cesium carbonate ($Cs_2O_3$) as base in N,N-dimethylformamide (DMF) as solvent to give corresponding alkylated deuterated compound 6. (Dhanoa, D. S. et. al., *J. Med. Chem.* 1993, 36, 3788-3742). After completion of the reaction, it is quenched with cold water. Then, the reaction is diluted with methylene chloride and washed with brine. The organic phase is dried over anhydrous magnesium sulfate, filtered and concentrated under vacuum. The residue obtained as such is purified by flash chromatography (silica gel, ethyl acetate hexanes) to isolate purified alkylated deuterated compounds 6. Treatment of acetylacetone or Scheme 1: Synthesis of Deuterated Compound Intermediates (R = D, H)

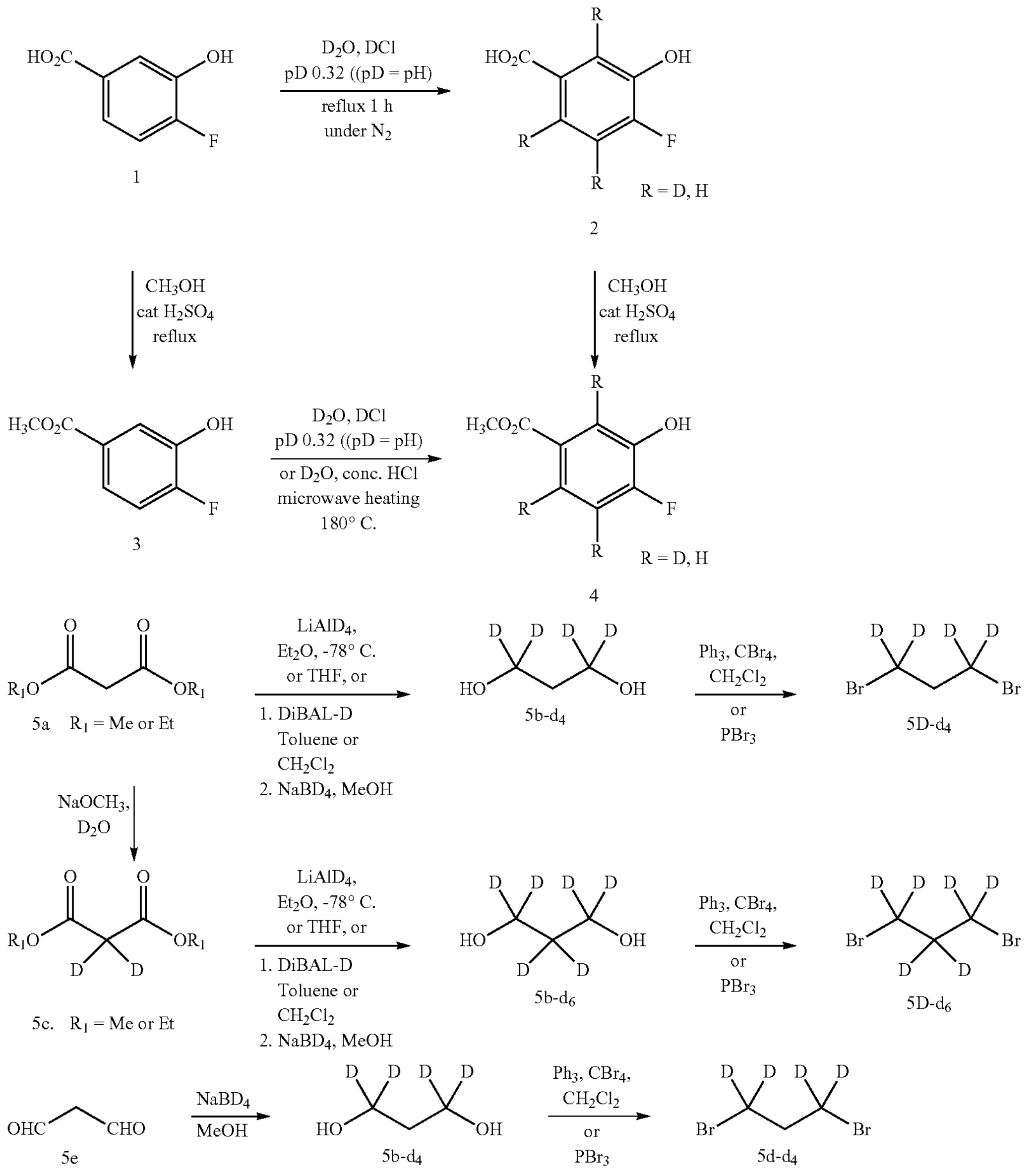

Synthesis of compounds of formula I of this invention is further shown in Scheme 2 given below. Deuterated methyl benzoate 4 is alkylated with deuterated 1,3-dibromopropane deuterated acetyl acetone compounds 8 with an organic base 1,8-diazabicyclo[5.4.0]undec-7-ene (DBU) in benzene and advanced intermediate compounds 6 produces the further alkylated penultimate intermediate 9. Treatment of the diketo derivatives 9 with hydrazine sulfate in 10% aqueous solution of sodium hydroxide (NaOH) gives the deuterated pyrazoles 10 [Wiley, R. H., et al., 3,5-Dimethylpyrazole. *Org. Synth.* 1951, 31, 43]. Saponification of the deuterated methyl ester product 10 with either aqueous solution of NaOH or LiOH in THE produces the corresponding pyrazolocarboxylic acid product 11.

Reactions are monitored by thin-layer chromatography (TLC) carried out on 0.20 mm POLYGRAM® SIL silica gel plates (Art.-Nr. 805 023) with fluorescent indicator UV254 using UV light as a visualizing agent. Normal phase flash column chromatography is carried out using Davisil® silica gel (100-200 mesh, Fisher). Wild type TTR concentration is serum, is measured at Stanford Medical School using nephelometric analyzer (28 mg/dL or 5 μM).

Scheme 2

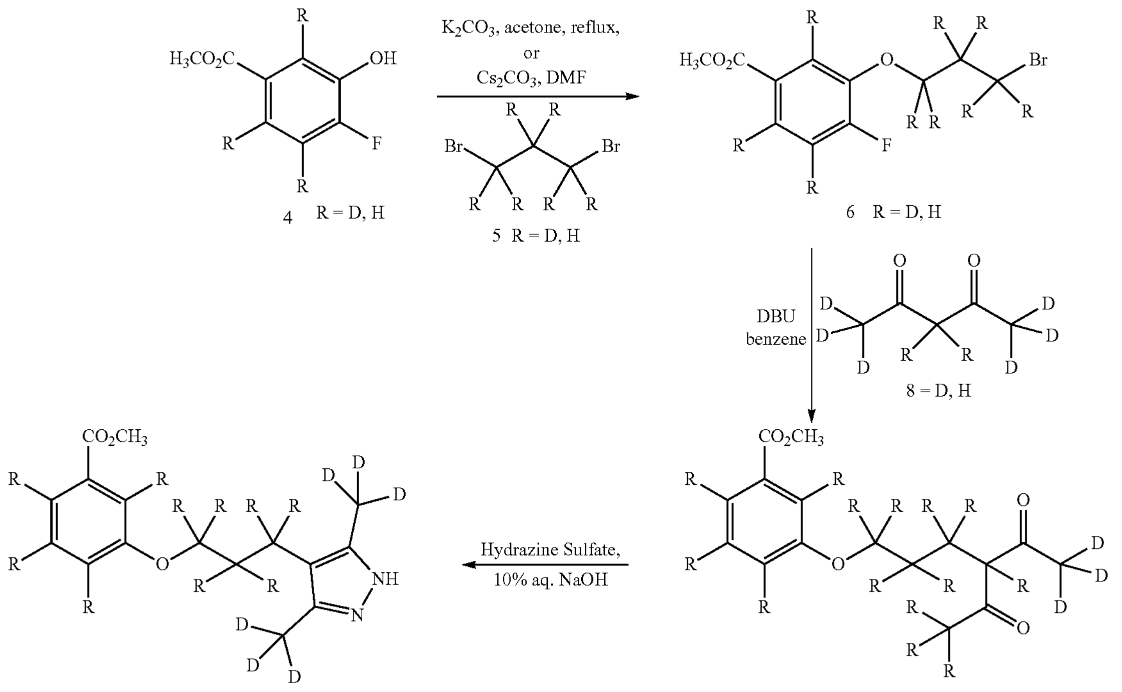

4 R = D, H

5 R = D, H

6 R = D, H

8 = D, H

9 R = D, H

10 R = D, H

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, s or see, second(s); min, minute(s); h or hr, hour(s); Room Temperature, RT, rt, etc.

Materials and Methods

Reagents and Instruments.

Prealbumin from human plasma (human TTR) is purchased from Sigma. Diflunisal, Thyroxine (T4), and resveratrol are purchased from Fisher. All reactions are carried out under argon atmosphere using dry solvents under anhydrous conditions, unless otherwise noted. The solvents used are ACS grade from Fisher. Reagents are purchased from Aldrich and Acros, and used without further purification.

Preparation of Deuterated 4-Fluoro-3-hydroxybenzoic acids 2:

Deuterium oxide ($D_2O$, 100 g, 5 moles) is added to 4-Fluoro-3-hydroxybenzoic acid (1 g, 6.4 mmol). Then deuterium chloride (DCl) is added to the mixture to adjust the pD (pH) of the reaction mixture to 0.32 and the resulting mixture is refluxed under nitrogen ($N_2$) for 1-2 h. The resulting mixture is lyophilized to remove $D_2O$ and DCI to yield the deuterated 4-fluoro-3-hydroxy benzoic acid 2 (0.9 g) in high yield. Compounds are characterized by NMR and/or MS.

Preparation of Methyl 4-Fluoro-3-hydroxybenzoate 3:

A catalytic amount of concentrated $H_2SO_4$ is added to a stirred solution of 4-Fluoro-3-hydroxybenzoic acid 1 (5 g, 32 mmol) in anhydrous methanol and the reaction mixture refluxed overnight. Methanol is removed in vacuo and the residue dissolved in a mixture of methylene chloride, ether and ethyl acetate. The organic phase is concentrated using rotary evaporator and the resulting ester is purified by flash column chromatography over a short column packed with silica gel and using mixture of EtOAc/Hexane as eluent to yield the desired methyl ester product 3 (5.1 g, 95%).

Use of ethanol ($CH_3CH_2OH$) instead of methanol ($CH_3OH$) provides the ethyl ester. Also, the use of HCl instead of $H_2SO_4$ produces the methyl or the ethyl ester when the mixture is refluxed in methanol or ethanol respectively.

Deuterated Methyl 4-Fluoro-3-hydroxybenzoate 4 from 2:

A catalytic amount of concentrated $H_2SO_4$ is added to a stirred solution of deuterated 4-Fluoro-3-hydroxybenzoic acids 2 (0.5 g, 3.16 mmol) in anhydrous methanol and the reaction mixture refluxed and the reaction monitored by TLC for rapid completion. Immediately after esterification, methanol is removed in vacuo and the residue dissolved in a mixture of methylene chloride, ether and ethyl acetate. The organic phase is concentrated and purified by flash column chromatography using a column packed with silica gel and using a solvent mixture of EtOAc/Hexane as eluent to yield deuterated 4-fluoro-3-hydroxy benzoic acids 4 (0.47g).

Deuterated Methyl 4-Fluoro-3-hydroxybenzoate 4 from 3:

Deuterium oxide ($D_2O$, 100 g, 5 moles) is added to Methyl 4-Fluoro-3-hydroxybenzoate 3 (1.1 g, 6.4 mmol). Then deuterium chloride (DCl) is added to the mixture to adjust the pD (pH) of the reaction mixture to 0.32 and the resulting mixture is refluxed under nitrogen ($N_2$) for one to two hours. The resulting mixture is lyophilized to remove $D_2O$ and DCI to give deuterated methyl 4-fluoro-3-hydroxy benzoate 4 in high yield.

Deuterated Methyl 4-Fluoro-3-hydroxybenzoic acids 4 from 3:

Microwave irradiation at 180 °C of a mixture of 3 (1 g, 5.8 mmol), 2 mL of deuterium oxide ($D_2O$ ), and concentrated HCl (1 equivalent) is heated at 180 °C for a half hour in a microwave apparatus. The reaction mixture is basified with NaOH, diluted with solvent methylene chloride ($CH_2Cl_2$) followed by a small amount of saturated aqueous solution of sodium chloride. The organic phase is separated and the remaining aqueous phase is further extracted twice with $CH_2Cl_2$. The combined $CH_2Cl_2$ portions are dried over $Na_2SO_4$, concentrated in vacuo and purified by flash chromatography to afford deuterated methyl 4-fluoro-3-hydroxybenzoate 4.

Deuterated 1,3-propanediol-$d_4$5b-$d_4$.

To a stirred solution of dimethyl malonate 5a (10 g, 0.075 mole) in diethyl ether at −78 °C is added a THF solution of lithium aluminum deuteride-$d_4$ (2.5 equivalent, LiAlD4) and reaction monitored for completion. Upon completion, the reaction is worked up and crude product is passed through a pad of celite and then through a short column of silica gel (Flash chromatography) to give 1,3-propanediol-$d_4$5b (5.2 g, 86%).

Deuterated propanediol 5b is also prepared by an alternative method as described here and illustrated in scheme 1. To a stirred solution of dimethyl malonate 5a (6 g, 0.045 mole) in ether (Et20) is added a solution of diisobutylaluminum deuteride (DIBAL-D, 4.5 equivalent) in toluene or methylene chloride, and mixture stirred until completion of reaction. After workup of the reaction mixture the crude deuterated dialdehyde product obtained as such is subjected to its further reduction by sodium borodeuteride ($NaBD_4$). To a solution of deuterated dialdehyde intermediate in methanol is added $NaBD_4$ (2.2 equiv, 0.165 mole) and the mixture stirred. Upon completion, the reaction is worked up and the product is purified by flash chromatography over silica gel to yield 5b-$d_4$ (3 g, 83%).

Deuterated 1,3-dibromopropane-$d_4$5d-$d_4$.

To a stirred solution of 1,3-propane-diol 5b (5 g, 0.0625 mole) in methylene chloride at 0 °C is added carbon tetrabromide ($CBr_4$, 2 equiv). To the mixture is added triphenyl phosphine ($PPh_3$, 2.02 equiv). After a few hours, the reaction mixture is slowly quenched by addition water. The organic phase is separated from aqueous portion, The aqueous portion is further extracted with methylene chloride. All organic extracts and portions are combined, washed with brine, dried over sodium sulfate, concentrated over rotatory evaporator to a residue which is purified to yield the deuterated 1,3-dibromopropane-$d_4$5$d_4$. (11.5 g, 89%).

Deuterated 1,3-dibromopropane 5d-$d_4$.

To a solution of deuterated 1,3-propanediol 5b-$d_4$ (5 g, 0.0625 mole) in diethyl ether (25 mL) at 0°-5 °C is added a solution of phosphorus tribromide ($PBr_3$, 17 g, 0.0628 mole, 1 equiv) in diethylether (40 mL) and the resulting reaction mixture allowed to stand initially and then stirred gently and slowly for 1-2 hours. The reaction is quenched by careful addition of 50 mL of saturated sodium bicarbonate ($NaHCO_3$) aqueous solution and 50 mL of water. The organic and aqueous layers are separated and the aqueous layer extracted once with ether. The combined organic phase is washed once with saturated aqueous solution of $NaHCO_3$, 10% sodium bisulfite ($Na_2SO_3$) aqueous solution, brine (aq NaCl), and then dried over anhydrous magnesium sulfate ($MgSO_4$), and filtered through a pad of silica. The solution is concentrated to 12g of a pale yellow oil, 5d-$d_4$, in 93% yield.

Dideuterated Dimethyl Malonate 5c:

To a mixture of dimethyl malonate (10 g, 0.075 mole) and deuterated water ($D_2O$ ) is added sodium methoxide ($CH_3ONa$, 8.2 g, 0.151 mole, 2 equiv) and the mixture stirred gently and slowly for 1-2 h. The progress of the reaction (enolization/deuteration and its completion may be monitored by NMR. Concentration of the reaction mixture using rotary evaporator yields dideuterated dimethyl malonate 5c (Scheme 1).

By using the same method as described above, using diethyl malonate (10 g, 0.0624 mole), $D_2O$ and sodium ethoxide (EtONa, 2 equiv) produces the corresponding alpha-dideuterated ethylmalonate 5c (Scheme 1).

Both deuterated methyl and/or ethyl compounds 5c are used without further purification in the next step of their reduction to the corresponding deuterated 1,3-propanediol 5b-$d_6$.

Deuterated 1,3-propanediol-$d_4$5b-$d_6$:

To a stirred solution of dideutertaed dimethyl malonate 5c (5 g, 0.0373 mole) in diethyl ether at −78 °C is added a THF solution of lithium aluminum deuteride-$d_4$ (2.5 equivalent, $LiAlD_4$) and reaction monitored for completion. Upon completion, the reaction is worked up and gave 1,3-propanediol-$d_6$5b-$d_6$ (2.5g).

Deuterated propanediol 5b-$d_6$ is also prepared by an alternative method as described here and illustrated in scheme 1. To a stirred solution of dimethyl malonate 5c (5 g, 0.0373 mole) in ether ($Et_2O$) is added a solution of diisobutylaluminum deuteride (DIBAL-D, 4.5 equivalent) in toluene or methylene chloride, and mixture stirred until completion of reaction. After workup of the reaction mixture the crude deuterated dialdehyde product obtained as such is subjected to its further reduction by sodium borodeuteride ($NaBD_4$). To a solution of deuterated dialdehyde intermediate in methanol is added $NaBD_4$ (2.2 equiv, 0.165 mole) and the mixture stirred. Upon completion, the reaction is worked up and the crude product is passed through plug of celite and short column of silica gel to yield 5b-$d_6$ (2.4 g).

Deuterated 1,3-dibromopropane-$d_4$5d-$d_6$:

To a stirred solution of 1,3-propane-diol 5b-$d_6$ (2.0 g, 0.024 mole) in methylene chloride at 0 °C is added carbon tetrabromide ($CBr_4$, 2 equiv). To the mixture is added triphenyl phosphine ($PPh_3$, 2.02 equiv). After a few hours, the reaction mixture is slowly quenched by addition of water. The organic phase is separated from aqueous and the aqueous phase is further extracted with methylene chloride. All $CH_2Cl_2$ extracted portions are combined, washed with brine, dried over sodium sulfate, concentrated over rotatory evaporator to a residue that is purified by flash chromatograthy using a short colum of silica gel using ethyl acetate/hexane mixture as the elution solvent to yield the deuterated 1,3-dibromopropane-$d_6$5$d_6$. (4.5 g, 90%).

Deuterated 1,3-dibromopropane 5d-$d_6$ using PBr3:

To a solution of deuterated 1,3-propanediol 5b-$d_4$ (4 g, 0.0488 mole) in diethyl ether (20 mL) at 0°-5 °C is added a solution of phosphorus tribromide ($PBr_3$, 14 g, 0.05 mole, 1.06 equiv) in diethylether (50 mL) and the resulting reaction mixture allowed to stand initially and then stirred gently and slowly for 1-2 hours. The reaction is quenched by careful addition of 50 mL of saturated sodium bicarbonate ($NaHCO_3$) aqueous solution and 50 mL of water. The organic and aqueous layers are separated and the aqueous layer extracted once with ether. The combined organic phase is washed once with saturated aqueous solution of $NaHCO_3$, 10% sodium bisulfite ($Na_2SO_3$) aqueous solution, brine (aq NaCl), and then dried over anhydrous magnesium sulfate ($MgSO_4$), and filtered through a pad of silica. The solution is concentrated to 9.5 g of a pale yellow oil, 5d-$d_6$, in 93.7% yield.

Deuterated 1,3-propanediol-$d_4$5b-$d_4$:

Deuterated 1,3-propanediol-$d_4$, 5b-$d_4$ is also prepared by reduction of malonaldehyde, $CH_2(CHO)_2$, 5e (Scheme1) with sodium deuteride ($NaBD_4$) in methanol. Since malonaldehyde has limited short shelf life, it is commercially available in its more stable bis-dimethylacetal derivative from Sigma-Aldrich. To a stirred mixture solution of malonaldehyde bis-dimethylacetal (3 g, 0.018 mole) in acetone is added Iodine (10 mol % $I_2$, 0.46 g) and stirred for 5-10 min at room temperature [Sun, J et al. Highly efficient chemoselective Deprotection of O,O-acetals and O,O-ketals catalyzed by molecular iodine in acetone. *J. Org. Chem.* 2004, 69, 25, 8932-8934]. Rapid removal of acetone by rotary evaporator gives free in situ malonadehyde which is immediately subjected to reduction by sodium deuteride in methanol. Methanol is added to malonadehyde followed by addition sodium borodeuteride ($NaBD_4$, 3 g, 0.0716 mole) and the reaction mixture stirred for 2 hours and then quenched with water. The reaction contents are diluted with organic solvent ether and/or ethyl acetate. Organic phase is separated and the aqueous phase further extracted twice with ether or ethyl acetate and organic phases combined, washed with brine, dried over anhydrous $Na_2SO_4$, and concentrated using rotary evaporator to yield deuterated 1,3-propanediol 5b-$d_4$.

Bis-dimethylacetal of malonaldehyde is also converted to free malonaldehyde in situ by hydrolysis by treating bis-dimethylacetal of malonaldehyde with aqueous HCl and then subjected to $NaBD_4$ reduction to 5b-$d_4$.

Deuterated 1,3-dibromopropane-$d_4$5d-$d_4$:

To a stirred solution of 1,3-propane-diol 5b-$d_4$ (2.0 g, 0.024 mole) in methylene chloride at 0 °C is added carbon tetrabromide ($CBr_4$, 2 equiv). To the mixture is added triphenyl phosphine ($PPh_3$, 2.02 equiv). After a few hours, the reaction mixture is slowly quenched by addition of water. The organic phase is separated from aqueous and the aqueous phase is further extracted with methylene chloride. All $CH_2Cl_2$ extracted portions are combined, washed with brine, dried over sodium sulfate, concentrated over rotatory evaporator to a residue that is purified by flash chromatograthy using a short column of silica gel using ethyl acetate/hexane mixture as the elution solvent to yield the deuterated 1,3-dibromopropane-$d_6$5$d_6$. (4 g).

Deuterated Acetylacetone (2,4-Pentanedione) 8:

To a solution of acetylacetone, 7 (5 g, 0.05 mole), in THF (15 mL) at −78 °C (using a dry dry ice-acetone bath) under argon is added 2 M solution of lithium diisopropylamide (LDA, 10 equiv) in THF and the mixture stirred. Deuterium oxide ($D_2O$, 10 g) is added in excess of 10 equivalent and mixture stirred for 30 min and the allowed to warm slowly to −20 °C and then 0 °C and then RT over a period of another one hour. The reaction mixture is quenched by pouring into 1N HCl solution and stirred. This mixture is diluted with ether, layer separated and theaqueous layer is further extracted twice with ether. The combined ethereal extract are sequentially washed with saturated aqueous $NaHCO_3$ solution, brine (aq NaCl solution) and the organic phase dried over $MgSO_4$, concentrated by using rotary evaporator to yield deuterated acetylacetone (2,4-pentanedione, 8) in high yield (5.2 g, 96%). Deuterium chloride (DCl) is also used instead of D20 for preparation of the deuterated acetylacetone (2,4-pentanedione-$d_8$ or 4-pentanedione-$d_6$) using LDA/DCl in THE as shown in Scheme 1.

Deuterated Methyl 3-(3-bromopropoxy)-4-fluorobenzoate 6:

To a stirred solution of methyl 4-fluoro-3-hydroxybenzoate 4 (1 g, 0.0059 mole) and deuterated, 1,3-dibromopropane 5d (1.2 g, 0059 mol, 1 equiv) in acetone (10 mL) is added potassium carbonate, ($K_2CO_3$,1.1 g, 0.008 mole). The reaction mixture is refluxed for 2.5 hours and then allowed to cool down to room temperature and further stirred overnight. The mixture is filtered and the solid washed with acetone. The filtrate is concentrated to yield product 6 (1.7 g, 96%).

Various deuterated analogs of compound 6 are prepared from their corresponding precursor compounds 4 according the above procedure ($K_2CO_3$, acetone, reflux).

Deuterated compounds 6 are also synthesized from the corresponding precursor compounds methyl 4-fluoro-3-hydroxy benzoates, 4, by their alkylation with various 1,3-dibromopropanes, 5, by using cesium carbonate in DMF ($Cs_2CO_3$, DMF) synthetic method.

Deuterated 3-[3-(2-fluoro-5-carbomethoxy)phenoxy)propyl]pentane-2,4-dione, 9:

To a stirring solution of deuterated acetylacetone (2,4-pentanedione-$d_8$ or $d_6$, 8, 0.73 g, 6.74 mmol, 2 equiv) and 1,8-diazabicyclo[5.4.0]undec-7-ene (DBU, 1.02 g, 6.74 mmol, 2 equiv) in benzene (8 mL) is added dropwise a solution of deuterated intermediate compound 6 (1 g, 3.365 mmol, 1equiv) in benzene (3.5 mL) and the resulting reaction mixture stirred for 72 hours at RT. The mixture is filtered, concentrated and the resulting residue is purified by flash column chromatography using silica gel column and EtOAc/hexanes solvent mixture as eluent to produce alkylated product, deuterated compound 9 (0.8 g, 76%), Deuterated 3,5-dimethyl-4 [3-(2-fluoro-5-carbomethoxy) phenoxy)propyl]pyrazole, 10:

To a solution of hydrazine sulfate (0.5 g, 3.8 mmol) in 6.5 mL of 10% sodium hydroxide at 0°-5° (using ice bath) is added compound 9 (0.8 g, 2.53 mmol) from above step with stirring [Wiley, R. H., et al. *Org. Synth.* 1951, 31, 43]. THF or ether (2 mL) is added to the reaction mixture and stirred for 1 hour. The reaction mixture is diluted with 5 mL of water and 25 mL of ether. The aqueous phase is extracted four times with ether (4×10 mL). The ether extracts are combined, washed once with sodium chloride solution, and dried over anhydrous potassium carbonate or sodium sulfate, filtered and filtrate concentrated. The resulting residue is purified by flash column chromatography over silica gel column (gradient methanol/$CH_2Cl_2$) to give the deuterated product, pyrazole 10 (0.6 g, 75%); Mass Spec. (m/z): $C_{16}H_7D_{12}FN_2O_3+H^+=319.2133$ $(M+H^+)$.

Deuterated 3-(3-(3,5-Dimethyl-1H-pyrazol-4-yl) propoxy)-4-fluorobenzoic acid, 11:

To a mixture of deuterated methyl ester 10 (0.16 g, 0.5 mmol) and 10 mL of THF and water (1;1, v/v) at 0 °C (ice bath) is added aqueous solution of sodium hydroxide (40 mg, 1 mmol, 2 equiv) and the mixture stirred for 1 hour and for additional 1 hour at RT to ensure completion of ester saponification to carboxylic acid. A solution of 1N aqueous HCl is added and the acidified mixture is then extracted three times with 40 mL of ethyl acetate (3×40 mL). The combined organic extracts were dried over sodium sulfate and concentrated using rotary evaporator to give the product, 3-(3-(3,5-bis(methyl-$d_3$)-1H-pyrazol-4-yl)propoxy-1,1,2,2,3,3-$d_6$)-4-fluorobenzoic acid, 11 (120 mg, 79% yield) as a white solid; Mass Spec. (m/z): $C_{15}H_5D_{12}FN_2O_3+H^+$=304.1976 (M+$H^+$).

BIOLOGICAL ASSAYS

Biological assays and methods for evaluating the activity of compounds of the present invention of formula I, and their pharmaceuticals salts, to increase the stability of tetrameric protein transthyretin (TTR) thereby preventing it from misfolding, aggregating, and depositing into organs and tissues and forming TTR amyloid are described below.

Binding Affinity Assay of Compounds to TTR

The binding affinity of compounds of the present invention to Transthyretin (TTR) at physiological pH is determined using fluorescence polarization (FP) assay. Known TTR kinetic stabilizer compounds (TTR natural ligand $T_4$, tafamidis and acodamidis) are used as controls for comparison in this assay. The FP assay is a competitive assay that is used to determine ligand binding to TTR by determining displacement of a fluorescent probe from $T_4$-binding sites of TTR by test compounds, All test compounds bind to TTR (purified from human plasma) at 10 μM. Test compounds, are assayed in a multi-point dose-response FP assay (concentration range between 0.003 and 100 μM). Isothermal titration calorimetry (ITC) is used to determine the binding constants of test compounds to TTR and also to determine cooperativity between the two TTR $T_4$ sites. ITC measurements show high binding constant of test compounds in low nanomolar range, Analysis of the free energies associated with compounds shows high binding affinity and the dissociation constants show that compounds bind to TTR with negative cooperativity.

Transthyretin Amyloid Fibril Formation Assay

The test compounds are dissolved in DMSO at a concentration of 720 μM. A solution of 5 microliter of a test compound is added to 0.5 mL of a 7.2 μM TTR solution in 10 mM phosphate pH 7.6, 100 mM KCl, 1 mM EDTA buffer, allowing the compound to incubate with TTR for 30 min. 495 μL of 0.2 mM acetate pH 4.2, 100 mM KCl, 1 mM EDTA is added, to afford final protein and inhibitor concentrations of 3.6 μM each and a pH of 4.4. The mixture is then incubated at 37 °C for 72 h, after which the tubes are vortexed for 3 seconds and the optical density is measured at 400 nm. The extent of fibril formation is determined by normalizing each optical density by that of TTR without inhibitor, defined to be 100% fibril formation. Control solutions of each compound in the absence of TTR are also tested and none absorbed appreciably at 400 nm.

Isothermal Titration Calorimetry Assay

A 25 μM solution of a test compound (in 10 mM phosphate pH 7.6, 100 mM KCl, 1 mM EDTA, 8% DMSO,) is titrated into a 1.2 μM solution of TTR in an identical buffer using a Microcal MCS Isothermal Titration calorimeter (Microcal, Northampton, Mass.). An initial injection of 2 μL is followed by 25 injections of 10 μL at 25 °C. The thermogram is integrated and a blank is subtracted to yield a binding isotherm that fit best to a model of two identical binding sites using the ITC data analysis package in ORIGIN 5.0 (Microcal).

Isothermal Titration Calorimetry Assay

Calorimetric titrations are conducted on a VP-ITC calorimeter (MicroCal, Northampton, Mass.). A solution of test compound (a compound of the present invention, and Tafamidis) (25 μM in PBS pH 7.4, 100 mM KCl, 1 mM EDTA, 8% DMSO) is prepared and degassed for 0.25 hour, and then titrated into an isothermal titration calorimetry cell containing 2 μM of TTR in an identical buffer. Solutions of test compounds (8.0 μL each) are injected into the isothermal titration calorimetry cell at 25 °C to fully saturate TTR with ligand. Integration of the thermogram after the subtraction of blanks gives a binding isotherm that fit best to a model of two interacting sites exhibiting negative cooperativity. The data are fit by a nonlinear least squares approach with four adjustable parameters: $K_{d1}$, ΔH1, $K_{d2}$, and ΔH2 using the isothermal titration calorimetry data analysis module in MicroCal ORIGIN 5.0 software.

Isothermal Titration Calorimetry Assay

The thermodynamic parameters that characterize the binding of TTR ligands to WT-TTR are also determined using a MicroCal Auto-iTC200 calorimeter (MicroCal, Malvern-Panalytical), [Francisca, P., et al. *FEBS Journal,* 2021, 288, 310-324]. A 100 μM solution of a test compound (in a PBS buffer pH 7.0 containing 100 mM KCl, 1 mM EDTA and 2.5% DMSO) is titrated into an ITC cell containing a 5 μM solution of WT-TTR in the same buffer at 25 °C. A stirring speed of 750 rpm and 2 μL injections is programmed, with a 150 s equilibration period between each injection to allow the calorimetric signal (thermal power) to return to baseline and a 10 μcal/s reference power. Two independent titrations are done for each TTR ligand. The experimental data are analyzed with a general model for a protein with two ligand-binding sites [A unified framework based on the binding polynomial for characterizing biological systems by isothermal titration calorimetry, Vega, S., et al. *Methods* (*Amsterdam, Netherlands*), 2015, 76, 99-115; Isothermal titration calorimetry: general formalism using binding polynomials, Freire, E., et al., *Methods in Enzymology,* 2009, 455 (*Biothermodynamics, Part A*), 127-155] implemented in Origin 7.0 (OriginLab) accounting for cooperative and non-cooperative binding.

Urea-Induced TTR Tetramer Dissociation Kinetics

TTR solutions (1.8 μM in PBS) are incubated with different TTR ligands (3.6 μM) for 30 min at RT, and 6 M urea is added. DMSO is used as a control. The process of unfolding is tracked by intrinsic fluorescence spectroscopy using FP-8200 Spectrofluorometer (Jasco). Trp residues are excited at 295 nm, and emission spectra are collected from 310 to 400 nm. Trp exposure upon denaturation red shifts the wavelength of maximum fluorescence from approximately 335 to 355 nm. The 355/335 fluorescence emission intensity is normalized from minimum (100% folded) to maximum (0% folded) and plotted as a function of time. The TTR fluorescence of the control sample after incubation at RT for 96 h in 6 M urea is considered the maximum.

TTR In Vitro Aggregation Assay

The anti-aggregational activity of TTR ligands is evaluated using the established acid-mediated aggregation assay [Francisca, P., et al. *FEBS Journal,* 2021, 288, 310-324]. WT-TTR solutions (7 μM in 10 mM sodium phosphate, 100 mM KCl, 1 mM EDTA, 1 mM DTT, pH 7.0) are mixed with increasing concentrations of test compounds (prepared in 100% DMSO). The percentage of DMSO is adjusted to 5% (v/v) in the final reaction assay mixture. After incubating for 30 min at 37 °C, the pH of the samples is dropped to 4.2 by the addition of acetate buffer (100 mM sodium acetate, 100 mM KCl, 1 mM EDTA, 1 mM DTT, pH 4.2), and the solutions are further incubated for 72 h at 37 °C. The extent of TTR aggregation is determined by measuring turbidity at 340 nm using a Varian Cary Eclipse Fluorescence Spectrophotometer (Agilent Technologies). As some of the compounds present dose-dependent absorbance at 340 nm, each measurement is corrected with a buffer containing the same concentration of the test compound but lacking TTR. For each inhibitor concentration, the percentage of TTR aggregation is given by the ratio of the turbidity of the sample of interest to that of a control sample incubated without compound multiplied by 100%.

TTR Stabilization Studies by Isoelectric Focusing

Isoelectric focusing (IEF) under semi-denaturing conditions [Binding of epigallocatechin-3-gallate to transthyretin modulates its amyloidogenicity, Ferreira, N., *FEBS Letters,* 2009, 583, 3569-3576] is used to evaluate the stabilizing effect of test compound of the present invention on recombinant TTR and in plasma TTR. Recombinant WT-TTR is produced using an *Escherichia coli* bacterial expression system, as detailed elsewhere [Selective binding to transthyretin and tetramer stabilization in serum from patients with familial amyloidotic polyneuropathy by an iodinated diflunisal derivative, Almeida, M. R., et al. *Biochemical Journal,* 2004, 381, 351-356]. For the plasma assays, human plasma from control individuals (n=6), carrying WT-TTR (≈3.9 μM), is incubated ON at 4 °C with tafamidis, tolcapone, or test compound of the present invention at two different concentrations (19.5 and 39 μM). Similarly, recombinant WT-TTR (6 μM) is also treated ON at 4 °C with the same compounds at concentrations of 30 and 60 μM. DMSO (5%) is used as vehicle. Control samples are incubated in similar conditions without the compounds. After incubation, the samples are loaded into a native PAGE, and the gel band containing TTR is excised and applied to an IEF gel. The IEF gel contained 4 M urea (semi-denaturing conditions) and 5% (v/v) ampholytes, pH 4-6.5 (Sigma-Merck), and is run at 1200 V for 5 h. Proteins are fixed and stained with Coomassie blue. The gels are scanned using a GS-900 calibrated densitometer (Bio-Rad) and analyzed by densitometry using the QuantityOne software version 4.6.6 (Bio-Rad). The ratio of the TTR tetramer over total TTR (TTR tetramer+monomer) is calculated for each plasma sample, and the percentage of tetramer stabilization is calculated as ((ratio treated sample—ratio control sample)/ratio control sample)×100. Treated and control plasma samples come from the same donor.

$T_4$ Binding Competition Assay

Binding competition assays with radioactive $T_4$ (2-amino-3-(4-(4-hydroxy-3,5-diiodophenoxy)-3,5-diiodophenyl)propanoic acid) are performed by incubation of 5 μL of human plasma samples of WT-TTR carriers (n=4) with 1 μL of $[^{125}I]$-$T_4$ (specific radioactivity 1250 μCi/μg; concentration 320 μCi/mL; Perkin Elmer) in the presence of 39 μM compounds. The negative control is performed by addition of same amount of DMSO to samples. After 1 h incubation at RT, plasma proteins are fractionated by native PAGE [Transthyretin (prealbumin) in familial amyloidotic polyneuropathy: genetic and functional aspects, Saraiva, M. J., et al., *Advances in neurology,* 1988, 48, 189-200], and the gels are dried and exposed to an autoradiography film. The films are scanned, and the intensity of the bands is determined by densitometry using Image Lab software version 5.2.1 (Bio-Rad). The ratio of $T_4$ (2-amino-3-(4-(4-hydroxy-3,5-diiodophenoxy)-3,5-diiodophenyl)propanoic acid) bound to TTR over total $T_4$ (TBG+ALB+TTR) is calculated for each sample and normalized to the maximum value, which corresponds to the negative control sample.

Biological Activity of Test Compounds as Stabilizers of Both WT-TTR and V122I-TTR in Human Serum Against Acid-Mediated Dissociation and Amyloidogenesis The test compounds are tested for their ability to stabilize WT-TTR in human serum. TTR tetramer dissociation to monomers and subsequent aggregation occur very inefficiently at neutral pH. To measure the TTR stabilizing effect of test compounds, an acid-mediated tetramer dissociation assay is used. Test compounds (10 μM) are pre-incubated with human serum (TTR 5 μM) and the pH is lowered to pH 4.0 to induce aggregation. Aliquots, taken at 0 and 72 hours, are treated with glutaraldehyde to cross-link TTR tetramers that remained intact in the serum sample. SDS-PAGE followed by immunoblot analysis is used to measure the amount of intact TTR tetramer after 72 hours of acid treatment in the presence and absence of test compounds. Test compounds of the present invention are found to be highly effective stabilizers of serum WT-TTR. At 10 μM, test compounds of the present invention are also highly effective in nearly complete stabilization of the V122I-TTR mutant in serum samples.

Determination of Solubility of Compounds

Solubility of compounds is determined by addition of known and weighed amount of a compound of the present invention to a stirred distilled or deionized water until total complete dissolution. All experiments are performed in triplicate.

Cytotoxicity Assay

Cytotoxicity assays are performed to evaluate chemical toxicity of test compounds of the present invention to human cells. Two cell lines, HeLa and HepG2 cells, are cultured in MEM ALPHA (Gibco) and 10% FBS at 37 °C in 5% $CO_2$ humidified atmosphere. HeLa cells are seeded at 3500 cells/well and HepG2 cells at 4500 cells/well in 96-well plates and incubated with increasing concentrations of compound at a range of concentrations from 2 to 100 μM during 72 h at 37 °C. Controls are performed with the equivalent amount of DMSO relative to each concentration of compound diluted in MilliQ water. Then, cell viability is determined by addition of 10 μL of the PrestoBlue reagent (Thermo Fisher Scientific), and after an incubation period of 15 min at 37 °C, the fluorescence intensity is collected using a 590/20 filter with an excitation wavelength of 535 in a Victor3 Multilabel Reader (PerkinElmer). Experiments are carried out in triplicate, and the percentage of cell viability for each well is calculated as (intensity sample—mean intensity blank)/(mean intensity control—mean intensity blank)×100, where "mean intensity blank" corresponds to the mean intensity of wells with PrestoBlue alone and "mean intensity control" is the mean intensity of wells that contain the corresponding percentage of DMSO.

What is claimed is:

1. A deuterium-enriched compound selected from the group consisting of:

(a)

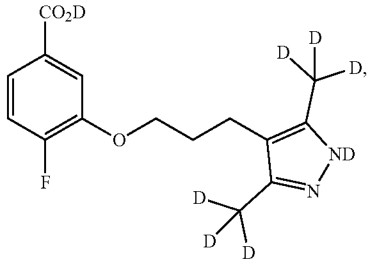

3-(3-(3,5-bis(methyl-$d_3$)-1H-pyrazol-4-yl-1-d)propoxy)-4-fluorobenzoic acid-d (b)

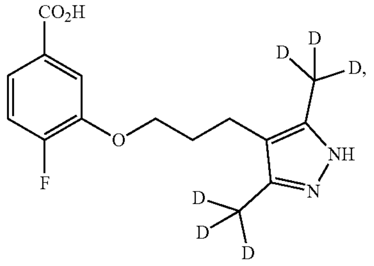

3-(3-(3,5-bis(methyl-$d_3$)-1H-pyrazol-4-yl)propoxy)-4-fluorobenzoic acid (c)

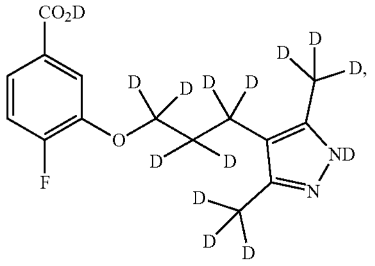

3-(3-(3,5-bis(methyl-$d_3$)-1H-pyrazol-4-yl-1-d)propoxy-1,1,2,2,3,3-$d_6$)-4-fluorobenzoic acid-d (d)

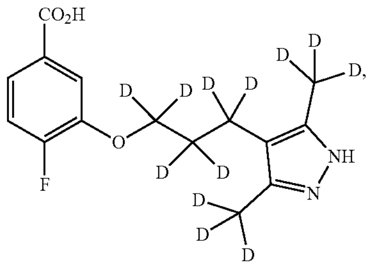

3-(3-(3,5-bis(methyl-$d_3$)-1H-pyrazol-4-yl)propoxy-1,1,2,2,3,3-$d_6$)-4-fluorobenzoic acid -continued (e)

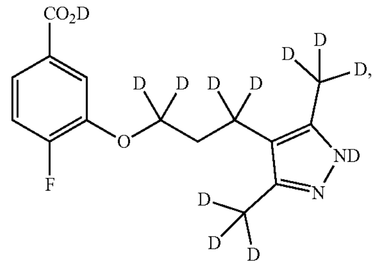

3-(3-(3,5-bis(methyl-$d_3$)-1H-pyrazol-4-yl-1-d)propoxy-1,1,3,3-$d_4$)-4-fluorobenzoic acid-d (f)

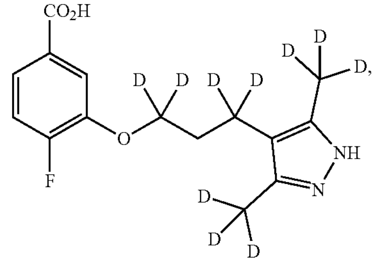

3-(3-(3,5-bis(methyl-$d_3$)-1H-pyrazol-4-yl)propoxy-1,1,3,3-$d_4$)-4-fluorobenzoic acid (g)

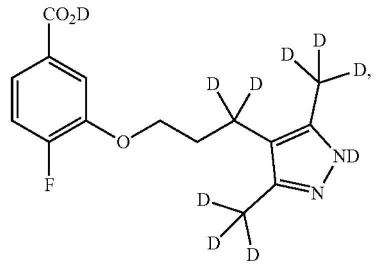

3-(3-(3,5-bis(methyl-$d_3$)-1H-pyrazol-4-yl-1-d)propoxy-3,3-$d_2$)-4-fluorobenzoic acid-d (h)

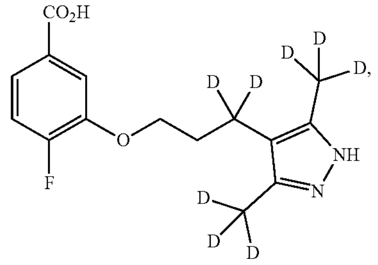

3-(3-(3,5-bis(methyl-$d_3$)-1H-pyrazol-4-yl)propoxy-3,3-$d_2$)-4-fluorobenzoic acid -continued (i)

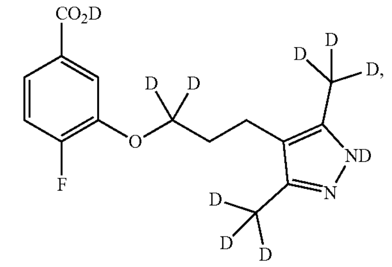

3-(3-(3,5-bis(methyl-$d_3$)-1H-pyrazol-4-yl-1-d)propoxy-1,1-$d_2$)-4-fluorobenzoic acid-d (j)

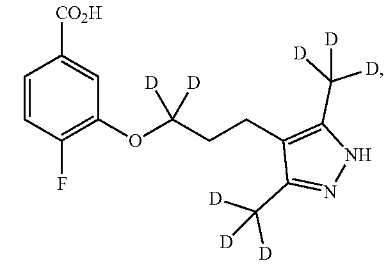

3-(3-(3,5-bis(methyl-$d_3$)-1H-pyrazol-4-yl)propoxy-1,1-$d_2$)-4-fluorobenzoic acid (k)

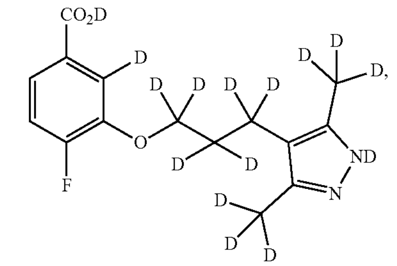

3-(3-(3,5-bis(methyl-$d_3$)-1H-pyrazol-4-yl-1-d)propoxy-1,1,2,2,3,3-$d_6$)-4-fluorobenzoic-2-d acid-d (l)

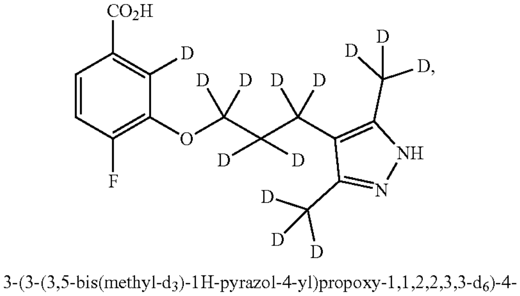

3-(3-(3,5-bis(methyl-$d_3$)-1H-pyrazol-4-yl)propoxy-1,1,2,2,3,3-$d_6$)-4-fluorobenzoic-2-d acid -continued (m)

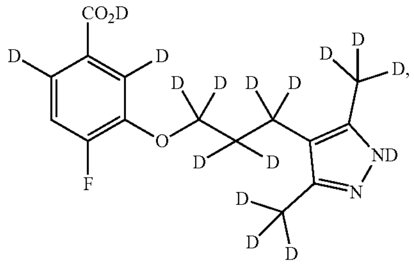

3-(3-(3,5-bis(methyl-$d_3$)-1H-pyrazol-4-yl-1-d)propoxy-1,1,2,2,3,3-$d_6$)-4-fluorobenzoic-2,6-$d_2$ acid-d (n)

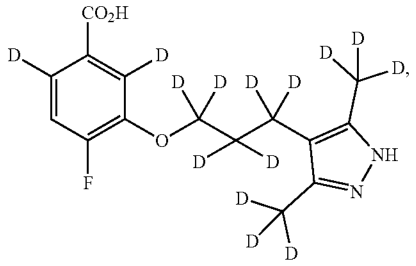

3-(3-(3,5-bis(methyl-$d_3$)-1H-pyrazol-4-yl)propoxy-1,1,2,2,3,3-$d_6$)-4-fluorobenzoic-2,6-$d_2$ acid (o)

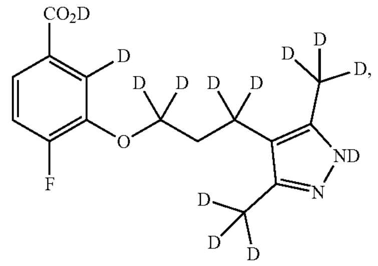

3-(3-(3,5-bis(methyl-$d_3$)-1H-pyrazol-4-yl-1-d)propoxy-1,1,3,3-$d_4$)-4-fluorobenzoic-2-d acid-d (p)

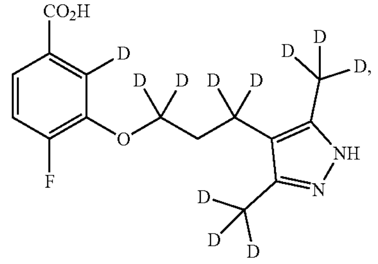

3-(3-(3,5-bis(methyl-$d_3$)-1H-pyrazol-4-yl)propoxy-1,1,3,3-$d_4$)-4-fluorobenzoic-2-d acid -continued (q)

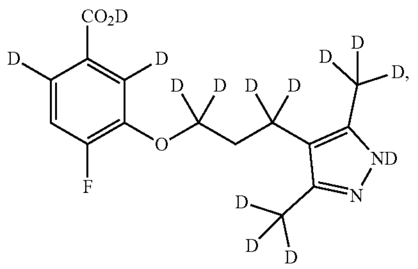

and 3-(3-(3,5-bis(methyl-$d_3$)-1H-pyrazol-4-yl-1-d)propoxy-1,1,3,3-$d_4$)-4-fluorobenzoic-2,6-$d_2$ acid-d (r)

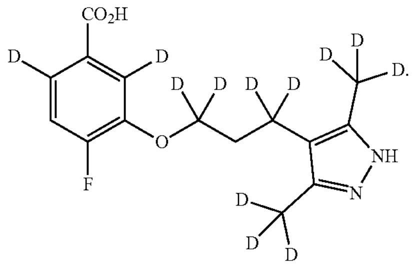

3-(3-(3,5-bis(methyl-$d_3$)-1H-pyrazol-4-yl)propoxy-1,1,3,3-$d_4$)-4-fluorobenzoic-2,6-$d_2$ acid

2. The compound of claim 1 selected from the group consisting of (a)

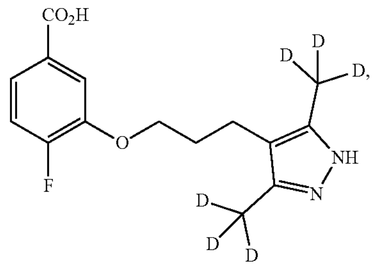

3-(3-(3,5-bis(methyl-$d_3$)-1H-pyrazol-4-yl)propoxy)-4-fluorobenzoic acid (b)

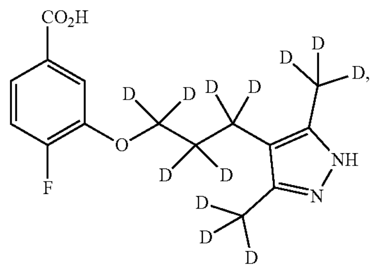

3-(3-(3,5-bis(methyl-$d_3$)-1H-pyrazol-4-yl)propoxy-1,1,2,2,3,3-$d_6$)-4-fluorobenzoic acid -continued (c)

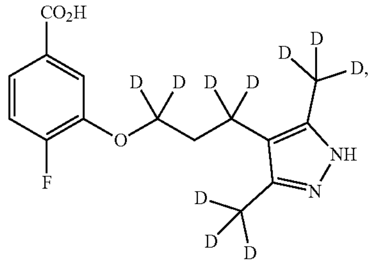

3-(3-(3,5-bis(methyl-$d_3$)-1H-pyrazol-4-yl)propoxy-1,1,3,3-$d_4$)-4-fluorobenzoic acid (d)

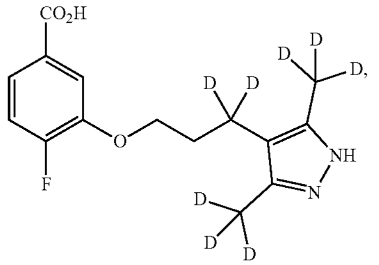

3-(3-(3,5-bis(methyl-$d_3$)-1H-pyrazol-4-yl)propoxy-3,3-$d_2$)-4-fluorobenzoic acid (e)

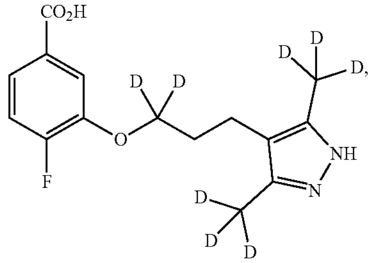

3-(3-(3,5-bis(methyl-$d_3$)-1H-pyrazol-4-yl)propoxy-1,1-$d_2$)-4-fluorobenzoic acid (f)

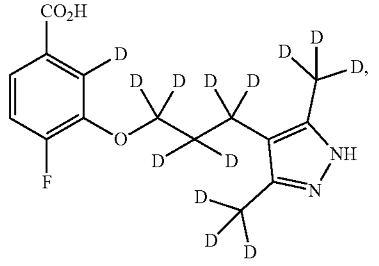

3-(3-(3,5-bis(methyl-$d_3$)-1H-pyrazol-4-yl)propoxy-1,1,2,2,3,3-$d_6$)-4-fluorobenzoic-2-d acid -continued (g)

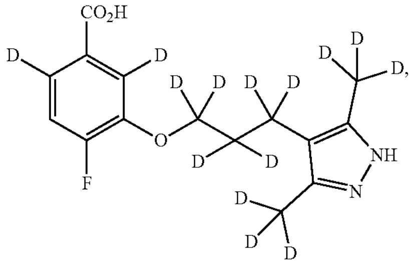

3-(3-(3,5-bis(methyl-d3)-1H-pyrazol-4-yl)propoxy-1,1,2,2,3,3-d6)-4-fluorobenzoic-2,6-d2 acid (h)

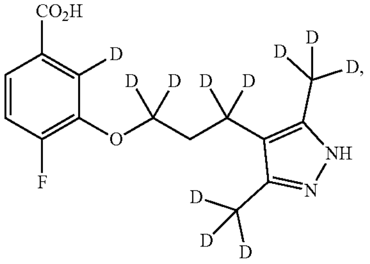

and 3-(3-(3,5-bis(methyl-d3)-1H-pyrazol-4-yl)propoxy-1,1,3,3-d4)-4-fluorobenzoic-2-d acid (i)

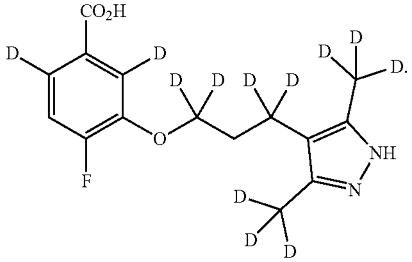

3-(3-(3,5-bis(methyl-d3)-1H-pyrazol-4-yl)propoxy-1,1,3,3-d4)-4-fluorobenzoic-2,6-d2 acid

3. The compound of claim 2 that is 3-(3-(3,5-bis(medyl-d$_3$)-1H-pyrazol-4-yl)propoxy)-4-flurobenzoic acid,

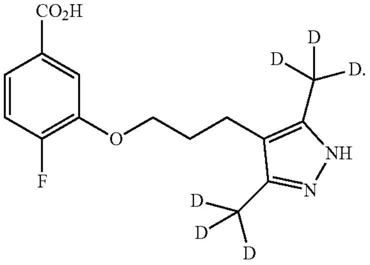

4. A pharmaceutical composition comprising a compound of claim 2 and a pharmaceutically acceptable carrier.

5. The pharmaceutical composition of claim 4 in an amount effective for the treatment of a disease selected from transthyretin amyloidosis cardiomyopathy (ATTR-CM), transthyretin amyloidosis polyneuropathy (ATTR-PN), neuropathy, senile systemic amyloidosis, cerebral amyloidosis, Alzheimer's disease, neuropathic amyloidosis, neuropathy, and gastrointestinal amyloidosis.

6. The pharmaceutical composition of claim 5 in an amount effective for the treatment of a disease selected from transthyretin amyloidosis cardiomyopathy (ATTR-CM), and transthyretin amyloidosis polyneuropathy (ATTR-PN).

7. A method of treating a disease selected from ATTR-CM, ATTR-PN, neuropathy, senile systemic amyloidosis, cerebral amyloidosis, neurophatic amyloidosis, neuropathy, and gastrointestinal amyloidosis, oculor amyloidosis, leptomeningeal amyloidosis, comprising administering a pharmaceutically effective amount of a compound of claim 2.

8. The method of claim 7, wherein the disease is selected from the group consisting of familial amyloid cardiomyopathy (ATTR-CM), familiar amyloid polyneuropathy (ATTR-PN), senile systemic amyloidosis, cerebral amyloidosis, neuropathic amyloidosis, neuropathy, and gastrointestinal amyloidosis, ocular amyloidosis, leptomeningeal amyloidosis, and wherein the compound is

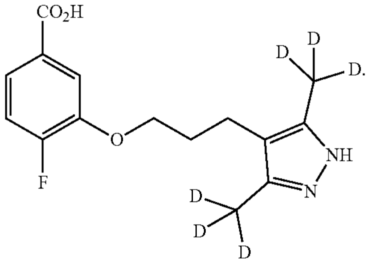

9. The method of claim 8, wherein the disease is familial amyloid cardiomyopathy (ATTR-CM).

10. The method of claim 8, wherein the disease is familial amyloid polyneuropathy (ATTR-PN).

11. The method of claim 8, wherein the disease is senile systemic amyloidosis.

12. The method of claim 8, wherein the disease is ocular amyloidosis.

13. The method of claim 8, wherein the disease is leptomeningeal amyloidosis.

* * * * *